US008926983B2

United States Patent
Nicolau et al.

(10) Patent No.: US 8,926,983 B2
(45) Date of Patent: Jan. 6, 2015

(54) METHOD FOR IMPROVING MEMORY IN AD PATIENTS

(75) Inventors: Yves Claude Nicolau, Newton, MA (US); Ruth Greferath, Kehl (DE); David Hickman, Saint-Sulpice (CH)

(73) Assignee: AC Immune SA, Lausanne (CH)

( * ) Notice: Subject to any disclaimer, the term of this patent is extended or adjusted under 35 U.S.C. 154(b) by 267 days.

(21) Appl. No.: 10/590,073

(22) PCT Filed: Feb. 22, 2005

(86) PCT No.: PCT/US2005/005285
§ 371 (c)(1),
(2), (4) Date: Jul. 17, 2007

(87) PCT Pub. No.: WO2005/081872
PCT Pub. Date: Sep. 9, 2005

(65) Prior Publication Data
US 2007/0281006 A1    Dec. 6, 2007

Related U.S. Application Data

(63) Continuation-in-part of application No. 10/958,211, filed on Oct. 4, 2004, now Pat. No. 8,663,650, which is a continuation-in-part of application No. 10/783,975, filed on Feb. 20, 2004, now abandoned.

(51) Int. Cl.
| | | |
|---|---|---|
| *A61K 39/00* | (2006.01) | |
| *C07K 14/47* | (2006.01) | |
| *C07K 16/18* | (2006.01) | |
| *A61K 39/385* | (2006.01) | |
| *A61K 9/127* | (2006.01) | |

(52) U.S. Cl.
CPC ......... *A61K 39/0007* (2013.01); *C07K 14/4711* (2013.01); *C07K 16/18* (2013.01); *A61K 9/127* (2013.01); *A61K 2039/6093* (2013.01); *A61K 39/385* (2013.01); *A61K 2039/55555* (2013.01)
USPC .................. 424/193.1; 424/184.1; 424/198.1; 424/278.1

(58) Field of Classification Search
None
See application file for complete search history.

(56) References Cited

U.S. PATENT DOCUMENTS

| | | | |
|---|---|---|---|
| 4,565,696 A | 1/1986 | Heath et al. | |
| 5,540,935 A | 7/1996 | Miyazaki et al. | |
| 5,672,662 A | 9/1997 | Harris et al. | |
| 5,721,106 A * | 2/1998 | Maggio et al. | 435/7.8 |
| 5,885,613 A * | 3/1999 | Holland et al. | 424/450 |
| 6,169,166 B1 | 1/2001 | Brun et al. | |
| 6,521,211 B1 | 2/2003 | Unger et al. | |
| 6,521,635 B1 | 2/2003 | Bates et al. | |
| 7,378,469 B2 | 5/2008 | Kozlowski | |
| 2002/0025312 A1 | 2/2002 | Tagawa et al. | |
| 2003/0108551 A1 | 6/2003 | Nicolau et al. | |
| 2004/0180002 A1 | 9/2004 | Young et al. | |
| 2004/0242845 A1 | 12/2004 | Nicolau et al. | |
| 2004/0248799 A1 | 12/2004 | Holaday et al. | |
| 2007/0032408 A1 | 2/2007 | Holmes et al. | |
| 2008/0233181 A1 | 9/2008 | Nagy et al. | |

FOREIGN PATENT DOCUMENTS

| | | |
|---|---|---|
| AU | 2004262471 A1 | 2/2005 |
| AU | 2004262472 | 2/2005 |
| EP | 0 203 676 B1 | 1/1992 |
| EP | 1270592 | 1/2003 |
| EP | 1 270 592 B1 | 9/2004 |
| JP | A H07-291853 | 11/1995 |
| JP | 8-501925 | 3/1996 |
| JP | A H11-152234 | 6/1998 |
| JP | 2002-500165 A1 | 7/1999 |
| JP | 2003-518151 | 6/2001 |
| JP | A 2002-47298 | 2/2002 |
| WO | WO 93/25700 A1 | 12/1993 |
| WO | WO 94/10198 A1 | 5/1994 |
| WO | WO 96/25435 A1 | 8/1996 |
| WO | WO 9625435 | 8/1996 |
| WO | WO 9846636 | 10/1998 |
| WO | WO 9927944 | 6/1999 |
| WO | WO 99/41279 A2 | 8/1999 |
| WO | WO 99/42130 | 8/1999 |
| WO | WO 0072876 | 12/2000 |
| WO | WO 00072880 | 12/2000 |
| WO | WO 01/18169 A2 | 3/2001 |
| WO | WO 0118169 | 3/2001 |

(Continued)

OTHER PUBLICATIONS

Medicine Net definition, Aug. 8, 2004, p. 1.*
Wikipedia, amyloid, 2009, p. 1-6.*
Wolf-Klein et al., Am Journal of Hosp Palliat Care, 2007, 24(1):77-82.*
Tagliavini et al. Journal of Virology, 2003, vol. 77, No. 15, p. 8462-8469.*
U.S. Appl. No. 11/038,501, Nov. 3, 2005, Tosi, et al.
U.S. Appl. No. 11/059,633, Nov. 17, 2005, Tosi, et al
U.S. Appl. No. 11/550,788, Jan. 31, 2008, Tosi, et al (Continued)

*Primary Examiner* — Yunsoo Kim
(74) *Attorney, Agent, or Firm* — F. Brent Nix; Johnson, Marcou & Isaacs, LLC

(57) ABSTRACT

The present invention comprises novel compositions and methods for eliciting high immune responses, of great specifity yielding conformationally sensitive antibodies. These antibodies recognize specific epitopes on a wide variety of antigens including but not limited to, amyloid protein, prion protein, $P_{170}$ glycoprotein. The novel compositions of the invention comprise supramolecular antigenic constructs generally comprising a peptide sequence, covalently attached to pegylated lysine resulting in modified and enhanced peptide presentation. The unique modification methodology of the present invention is applicable to a variety of peptides and can ultimately be employed in therapeutic formulations and vaccines for diseases and disorders such as Alzheimer's disease.

8 Claims, 14 Drawing Sheets

(56) References Cited

FOREIGN PATENT DOCUMENTS

| | | |
|---|---|---|
| WO | WO 0162284 | 8/2001 |
| WO | WO 02/21141 A2 | 3/2002 |
| WO | WO 0221141 | 3/2002 |
| WO | WO 02/09748 A1 | 7/2002 |
| WO | WO 02074243 | 9/2002 |
| WO | WO 03000719 | 1/2003 |
| WO | WO 03/015812 A2 | 2/2003 |
| WO | WO 03015812 | 2/2003 |
| WO | WO 03/039467 A2 | 5/2003 |
| WO | WO 03039467 | 5/2003 |
| WO | WO 2004013172 | 2/2004 |
| WO | WO 2004069182 | 8/2004 |
| WO | WO 2005/014036 A1 | 2/2005 |
| WO | WO 2005/081872 A2 | 9/2005 |
| WO | WO 2006/066003 A2 | 6/2006 |
| WO | WO 2007/068412 A2 | 6/2007 |
| WO | WO 2010/115843 A2 | 10/2010 |

OTHER PUBLICATIONS

U.S. Appl. No. 10/902,276, Aug. 11, 2005, Tosi, et al
U.S. Appl. No. 11/274,885, Oct. 19, 2005, Tosi, et al
Zhang, et al. "Multiple-Peptide Conjugates for Binding B-Amyloid Plaques of Alzheimer's Disease", Bioconjugate Chem. 2003, 14, 86-92.
Nicolau et al. "A liposome-based therapeutic vaccine against B-amyloid plaques on the pancrease of transgenic NORBA mice", PNAS, Feb. 19, 2002, vol. 99, No. 4.
Tosi et al. "Immune response against the murine MDRI protein induced by vaccination with synthetic lipopeptides in liposomes", Biochemical and Biophysical Research Communications, Jul. 17, 1995, vol. 212, No. 2.
C. Nicolau, R. Greferath, T.S. Balaban, Jr. Lazarte and R. Hopkins (2002). Proc. Natl. Acad. Sci. USA. 99,2332-2337.
Fluka AG (2002) Cat. # 79898.
P.-F. Tosi, D. Radu, and C. Nicolau (1995). Biochem. Biophys. Res. Chem. 212, 494-500.
Fukuda, et al., "Synthesis, Aggregation, and Neurotoxicity of the Alzheimer's AB1-42 Amyloid Peptide and Its Isoaspartyl isomers"; Bioorg. Med, Chem. Lett.; 9:953-956 (1999).
Petkova, et al.; "A structural model for Alzheimer's B-amyloid fibrils based on experimental constraints from solid state NMR"; Proc. Natl. Acad. Sci. USA; 99:16742-16747 (2002).
Medicine.Net definition, Aug. 8, 2004, p. 1.
Janssen, et al.; "Peptide-targeted PEG-liposomes in anti-angiogenic therapy"; International Journal of Pharmaceutics 254 (2003) 55-58.
Allen, et al.; "Liposomes containing synthetic lipid derivatives of poly(ethylene glycol) show prolonged circulation half-lives in vivo"; Biochimica et Biophysica Aeta, 1066 (1991) 29-36.
Pawlak-Roblin, et al.; "Inhibition of multidrug resistance by immunisation with synthetic P-glycoproteiin-derived peptides"; European Journal of Cancer 40 (2004) 606-613.
De Gioia, et al.; "Conformational Polymorphism of the Amyloidogenic and Neurotoxic Peptide Homologous to Residues 106-126 of the Prion Protein"; The Journal of Biological Chemistry, vol. 269, No. 11, Issue of Mar. 18, pp. 7859-7862, 1994.
Muhs, et al.; "Liposomel vaccines with conformation-specific amyloid peptide antigens define immune response and efficacy in APP transgenic mice"; 9810-9815, PNAS; Jun. 5, 2007, vol. 104, No. 23.
Muhs, et al.; "Improved Memory Capacity of Amyloid Precursor Protein Transgenic Mice Through Passive Administration of a Monoclonal Antibody Inducing a Conformational Shift of Amyloid-Beta"; The Journal of the Alzheimer's Association; vol. 2, No. 3, p. 21 (Jan. 7, 2006).
Gatouillat, et al.; "Immunization with liposome-anchored pegylated peptides modulates doxorubicin sensitivity in P-glycoprotein-expressing P388 cells"; Cancer Letters 257 (2007) 165, 171.

Grace, et al.; "Site of Pegylation and Polyethylene Glycol Molecule Size Attenuate Interferon-a Antiviral and Antiproliferative Activities through the JAK/STAT Signaling Pathway"; J. Bio. Chem., vol. 280, No. 8, pp. 6327-6336 (2005).
Pegasys Product Information, 2008, p. 1-51.
Kuby; "Vaccines" Immunology, Fourth Edition, Chapter 18, 2002, p. 449-465.
Office Action JP2006-554250, Dec. 15, 2010 (English Translation).
Bashir et al., "Generation of a Monoclonal Antibody to Pglcoprotein Peptides Using Tuberculin-PPD as a Carrier," Virchows Arch., 1998, vol. 432, pp. 279-287.
Candido et al., "Local Administration of Denditric Cells Inhibits Established Breast Tumor Growth: Implications for Apoptosis-Inducing Agents," Cancer Research, Jan. 1, 2011, vol. 61, pp. 228-236.
Chen et al., "Internal Duplication and Homology with Bacterial Transport Proteins in the MDR1 (P-Glycoprotein) Gene from Multidrug Resistant Human Cells," Cell, Nov. 7, 1986, vol. 47, No. 3, pp. 381-389.
Deprez et al., "Comparative Efficiency of Simple Lipopeptide Constructs for in Vivo Induction of Virus-Specific CTL," Vaccine, 1996, vol. 14, No. 5, pp. 375-382.
Endicott et al., "The Biochemistry of P-Glycoprotein-Mediated Multidrug Resistance," Annu. Rev. Biochem., 1989, vol. 58, pp. 137-171.
Fries et al., "Liposomal Malaria Vaccine in Humans: A Safe and Potent Adjuvant Strategy," Proc. Natl. Acad. Sci., Jan. 1992, vol. 89, pp. 358-362.
Frisch et al., "Synthesis of Short Polyoxyethylene-Based Heterobifunctional Cross-Linking Reagents. Application to the Coupling of Peptides to Liposomes," Bioconjugate Chemistry, 1996, vol. 7, No. 2, pp. 180-186.
Gaertner et al., "Site-Specific Attachment of Functionalized Poly(ethyleneglycol) to the Amino Terminus of Proteins," Bioconjugate Chem., 1996, vol. 7, pp. 38-44.
Juliano et al., "A Surface Glycoprotein Modulating Drug Permeability in Chinese Hamster Ovary Cell Mutants," Biochimica et Biophysica Acta, 1976, vol. 455, pp. 152-162.
Klohs et al., "Resistance to Anthrapyrazoles and Anthracyclines in Multidrug-Resistant P388 Murine Leukemia Cells: Reversal by Calcium Blockers and Calmodulin Antagonists," Cancer Research, Sep. 1986, vol. 46, pp. 4352-4356.
Mechetner et al., "Efficient Inhibition of P-Glycoprotein-Mediated Multidrug Resistance with a Monoclonal Antibody," Proceedings of the National Academy of Sciences of USA, Jul. 1, 1992, vol. 89, pp. 5824-5828.
Miller et al., "P-Glycoprotein Expression in Malignant Lymphoma and Reversal of Clinical Drug Resistance with Chemotherapy Plus High-Dose Verapamil," Journal of Clinical Oncology, Jan. 1991, vol. 9, No. 1, pp. 17-24.
Pierre et al., "In Vitro and in Vivo Circumvention of Multidrug Resistance by Servier 9788, a Novel Triazinoaminopiperidine Derivative," Investigational New Drugs, 1992, vol. 10, pp. 137-148.
Roberts et al., "Chemistry for Peptide and Protein PEGylation," Advanced Drug Delivery Reviews, 2002, vol. 54, pp. 459-476.
Schinkel et al., "Binding Properties of Monoclonal Antibodies Recognizing External Epitopes of the Human MDS1 P-Glycoprotein," Int. J. Cancer, 1993, vol. 55, pp. 478-484.
Schnolzer et al., "Constructing Proteins by Dovetailing Unprotected Synthetic Peptides: Backbone-Engineered HIV Protease," Science, New Series, Apr. 10, 1992, vol. 256, No. 5054, pp. 221-225.
Stober et al., "Synthesis of Characteristic Lipopeptides of the Human N-Ras Protein and their Evaluation as Possible Inhibitors of Protein Farnesyl Transferase," Bioorganic & Medicinal Chemistry, 1997, vol. 5, No. 1, pp. 75-83.
Stupp et al., "Ventricular Arrhythmia and Torsade de Pointe: Dose Limiting Toxicities of the MDR-Modulator S9788 in a Phase I Trial," Annals of Oncology, 1998, vol. 9, pp. 1233-1242.
Thiebault et al., "Cellular Localization of the Multidrug-Resistance Gene Product P-Glycoprotein in Normal Human Tissues," Proc. Natl. Acad. Sci. USA, Nov. 1987, vol. 84, pp. 7735-7738.
Tsuruo et al., "Circumvention of Drug Resistance with Calcium Channel Blockers and Monoclonal Antibodies," Drug Resistance in Cancer Treatment and Research, 1989, vol. 48, pp. 73-95.

(56) References Cited

OTHER PUBLICATIONS

Van Der Bliek et al., "Sequence of MDR3 cDNA Encoding a Human P-Glycoprotein," Gene, 1988, vol. 71, pp. 401-411.
Yang et al., "Treatment of Multidrug Resistant (MDR1) Murine Leukemia with P-Glycoprotein Substrates Accelerates the Course of the Disease," Biochemical and Biophysical Research Communications, 1999, vol. 266, pp. 167-173.
Japanese Office Action issued in JP Application No: 2006-554250, *JP Office Action*, pp. 1-10, Sep. 21, 2011.
Allen et al., Liposomes Containing Synthetic Lipid Derivatives of Poly(ehtylene glycol) Show Prolonged Circulation Half-lives in Vivo (Applicants only have Abstract) *Biochim Biophys Acta*, vol./Iss: 1066(1), pp. 29-36, Jul. 1, 1991.
Felix, Arthur, Site-Specific Poly (ethylene glycol)ylation of Peptides, *American Chemical Society—ACS Symposium Seminar*, vol. 680, pp. 218-238, Jan. 1, 1997.
Janssen et al., Peptide-targeted PEG-liposomes in Anti-angiogenic Therapy, *International Journal of Pharmaceutics*, vol. 254, pp. 55-58, Date: Jan. 1, 2003.
Kim, Yunsoo, Office Action issued in U.S. Appl. No: 10/958,211, *USPTO Office Action*, pp. 1-11, Jul. 16, 2010.
Kodera et al., Article in JP Office Action of Appl. No. 2006-554250— (for statement of relevance of English translation of Office Action attached hereto), *Tanpakushitsu Kakusan Koso (PNAS)*, vol./Iss. 48(11), pp. 1527-1533, Aug. 10, 2003.
Nicolau et al., A Liposome-Based Therapeutic Vaccine Against β-Amyloid Plaques on the Pancreas of Transgenic NORBA Mice, *Proceedings of the National Academy of Science*, vol./Iss: 99 (4), pp. 2332-2337, Feb. 19, 2002.
Office Action dated Jan. 20, 2012 for Chinese Application No. 2005800125877.
Abuchowski et al., "Alteration of Immunological Properties of Bovine Serum Albumin by Covalent Attachment of Polyethylene Glycol," The Journal of Biological Chemistry, 1977, vol. 252, No. 11, pp. 3578-3581.
Abuchowski et al., "Effect of Covalent Attachment of Polyethylene Glycol on Immunogenicity and Circulating Life of Bovine Liver Catalase," The Journal of Biological Chemistry, 1977, vol. 252, No. 11, pp. 3582-3586.
Gura, "Systems for Identifying New Drugs are Often Faulty," Science, 1997, vol. 278, pp. 1041-1042.
Kaiser, "First Pass at Cancer Genome Reveals Complex Landscape," Science, 2006, vol. 313, p. 1370.
Kodera et al., Proteins, Nucleic Acids and Enzymes, Aug. 10, 2003, vol. 48, No. 11, pp. 1527-1533.
Marincola et al., "Tumors as Elusive Targets of T-Cell Based Active Immunotherapy," Trends in Immunology, Jun. 2003, vol. 24, pp. 334-341.
English translation of Japanese Office Action dated Feb. 21, 2013 for Japanese Patent Application No. 2011-131772, pp. 1-6.
European Search Report and Written Opinion dated May 9, 2012 in co-pending European Patent Application No. 12153152.9, pp. 1-10.
Muhs, A. et al., "Improved Memory Capacity of Amyloid Precursor Protein Transgenic Mice Through Passive Administration of a Monoclonal Antibody Inducing a Conformational Shift of Amyloid-Beta," Alzheimer's & Dementia: The Journal of the Alzheimer's Association, Jul. 1, 2006, vol. 2, No. 3, p. S21.
Muhs, A. et al., "Liposomal Vaccines with Conformation-Specific Amyloid Peptide Antigens Define Immune Response and Efficacy in APP Transgenic Mice," Jun. 2007, Proceedings of the National Academy of Sciences of USA, vol. 104, No. 23, pp. 9810-9815.
Nicoloau, C. et al., "A Liposome-Based Therapeutic Vaccine Against Beta-Amyloid Plaques on the Pancreas of the Transgenic Norba Mice," Proceedings of the National Academy of Sciences of USA, Feb. 19, 2002, vol. 99, No. 4, pp. 2332-2337.
Solomon, B., "Immunological Approach for the Treatment of Alzheimer's Disease," Journal of Molecular Neuroscience, Jan. 1, 2003, vol. 20, No. 3, pp. 283-286.

Allen et al., Use of the Post-Insertion Method for the Formation of Ligand-Coupled Liposomes, *Cellular & Molecular Biology Letters*, vol. 7, pp. 889-894, Jan. 1, 2002.
Allison et al., Liposomes as Immunological Adjuvants, *Nature*, vol. 252, pp. 252 Nov. 15, 1974.
Alving et al., Liposomes as Carriers of Peptide Antigens: Induction of Antibodies and Cytotoxic T to Lymphocytes to Conjugated and Unconjugated Peptides, *Immunological Reviews*, vol. 145, pp. 1-27, Jan. 1, 1995.
Barret et al., Evaluation of Virology of Quinacrine Treatment for Prion Diseases, *Journal of Virology*, vol./Iss:77(13), pp. 8462-8469, Jan. 1, 2003.
Cussac, Y., International Report on Patentability and Written Opinion for PCT/EP2011/063933, pp. 1-7, Feb. 12, 2013.
Fieser et al., Influence of Protein Flexibility and Peptide Conformation on Reactivity of Monoclonal Anti-Peptide Antibodies with a Protein α-helix, *Proceedings of the National Academy of Science USA*, vol. 84, pp. 8568-8572, Dec. 1, 1987.
Fleiner et al., Studies on Protein-Liposome Coupling Using Novel Thiol-Reactive Coupling Lipids: Influence of Spacer Length and Polarity, *Bioconjugate Chemistry*, vol. 12, pp. 470-475, Jan. 1, 2001.
Frisch et al., Synthetic Peptide-Based Highly Immunogenic Liposomal Constructs, *Methods in Enzymology*, vol. 373, pp. 51-73, Jan. 1, 2003.
Frisch et al., Parameters Affecting the Immunogenicity of a Liposome-Associated Synthetic Hexapeptide Antigen, *European Journal of Immunology*, vol. 21, pp. 185-193, Jan. 1, 1991.
Guan et al., Liposomal Formulations of Synthetic MUC1 Peptides: Effects on Encapsulation versus Surface Display of Peptides on Immune Responses, *Bioconjugate Chemistry*, vol./Iss:9 (4), pp. 451-458, Jan. 1, 1998.
Kersten et al., Liposomes and ISCOMS as Vaccine Formulations, *Biochemica & Biophysica Acta*, vol. 1241, pp. 117-138, Jan. 1, 1995.
Kim, Y., Office Action issued in copending U.S. Appl. No. 10/958,211, filed Oct. 4, 2004, pp. 1-8, Dec. 18, 2009.
Kim, Y., Office Action issued in copending U.S. Appl. No. 10/958,211, filed Oct. 4, 2004, pp. 1-6 Date: Nov. 29, 2007.
Kim, Y., Office Action issued in copending U.S. Appl. No. 10/958,211, filed Oct. 4, 2004, pp. 1-8, Oct. 29, 2010.
Kim, Y., Office Action issued in copending U.S. Appl. No. 10/958,211, filed Oct. 4, 2004, pp. 1-12, Sep. 8, 2008.
Kim, Y., Office Action issued in copending U.S. Appl. No. 10/958,211, filed Oct. 4, 2004, pp. 1-8, Jul. 16, 2010.
Kim, Y., Office Action issued in copending U.S. Appl. No. 10/958,211, filed Oct. 4, 2004, pp. 1-12 Jun. 4, 2007.
Kim, Y., Office Action issued in copending U.S. Appl. No. 10/958,211, filed Oct. 4, 2004, pp. 1-12, May 8, 2009.
Kim, Y., International Search Report and Written Opinion—Appl. No: PCT/US05/05285, pp. 1-16, May 2, 2007.
Kim, Y., Office Action issued in copending U.S. Appl. No. 10/958,211, filed Oct. 4, 2004, pp. 1-10 Apr. 13, 2011.
Lu et al. A de Novo Designed Template for Generating Conformation-Specific Antibodies that Regcognize α-Helices in Proteins, *The Journal of Biological Chemistry*, vol./Iss:277 (26), pp. 23515-23524, Jun. 28, 2002.
Moreira et al., Use of the Post-Insertion Technique to Insert Peptide Ligands into Pre-Formed Stealth Liposomes with Retention of Binding Activity and Cytotoxicity, *Pharmaceutical Research*, vol./Iss:19 (3), pp. 265-269, Mar. 1, 2002.
O'Nuallian et al., Conformational Abs Recognizing a Generic Amyloid Fibril Epitope, *Porceedings of the National Academy of Sciences*, vol./Iss:99 (3), pp. 1485-1490, Feb. 5, 2002.
Schifferer, H., International Report on Patentability and Written Opinion issued in PCT/EP2011/068797, pp. 1-8, Apr. 30, 2013.
Schmechel et al., Alzheimer β-Amyloid Homodimers Facilitate Aβ Fibrillization and the Generation of Conformational Antibodies, *The Journal of Biological Chemistry*, vol./Iss:278 (37), pp. 35317-35324, Sep. 12, 2003.
Torchilin, V., Recent Advances with Liposomes as Pharmaceutical Carriers, Publ. *Nature Reviews*, vol. 4, pp. 145-160, Feb. 1, 2005.
Wolf-Klein et al., Conceptualizing Alzheimer's Disease as a Terminal Medical Illness (Abstract only), *American Journal of Hospital Palliative Care*, vol./Iss:24 (1), pp. 77-82, Feb. 1, 2007.

(56) References Cited

OTHER PUBLICATIONS

Office Action dated Sep. 5, 2013 for U.S. Appl. No. 11/550,788, pp. 1-6.

Boeckler et al., "Immunogenicity of New Heterobifunctional Cross-Linking Reagents Used in the Conjugation of Synthetic Peptides to Liposomes," Journal of Immunological Methods, 1996, vol. 191, pp. 1-10.

Raymond et al., "Mammalian Multidrug-Resistance Gene: Correlation of Exon Organization with Structural Domains and Duplication of an Ancestral Gene," Proc. Natl. Acad. Sci., Sep. 1989, vol. 86, pp. 6488-6492.

* cited by examiner

Chemically Modified β-amyloid Antigen

G-OH

Figure 2
Liposome Reconstituted, Chemically Modified Amyloid-Antigen

Multiple P$_{170}$ Antigen

Figure 4
Synthetic Peptides Used For This Study

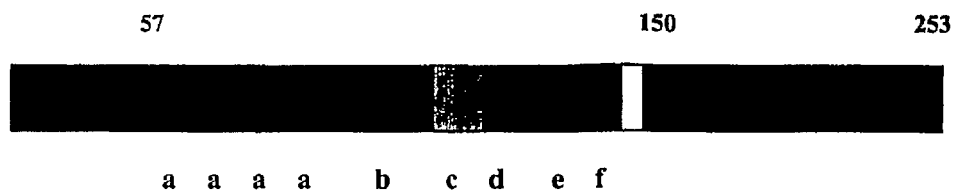

Fig. 4 : Synthetic peptides used for this study (single-letter amino-acid code)
a. PrP 57-64. WGQPHGGG b. PrP 89-106. WGQGGGTHSQWNKPSKPK: c. PrP 106-140. KTNMKHMAG: d. PrP 106-126. KTNMKHMAGAAAAGAVVGGLG: c. PrP 127-135. GYMLGSAMS: f. PrP 127-147. GYMLGSAMSRPIIHFGSDYED: g. PrP 106-126 scrambled. NGAKALMGGHGATKVMVGAAA: a-f. amino-acid sequence of peptides homologous to different fragments of the amyloid protein purified from GSS brains (residues 58 to ~ 150)[12]. g. Scrambled version of PrP 106-126. the octapeptide "a" is repeated for 4 or 5 times in the PrP sequence.

Aβ 4-11
Ac-Lys-Phe-Arg(Pbf)-His(Trt)-Asp(OtBu)-Ser(tBu)-Gly-Tyr(tBu)-Glu(OtBu)-Lys-Gly-OH

Aβ 1-16
Ac-Lys-Asp(OtBu)-Ala-Glu(OtBu)-Phe-Arg(Pbf)-His(Trt)-Asp(OtBu)-Ser(tBu)-Gly-Tyr(tBu)-Glu(OtBu)-Val-His(Trt)-His(Trt)-Gln(Trt)-Lys(Boc)-Lys-Gly-OH

Aβ 22-35
Ac-Lys-Glu(OtBu)-Asp(OtBu)-Val-Gly-Ser(tBu)-Asn(Trt)-Lys(Boc)-Gly-Ala-Ile-Ile-Gly-Leu-Met-Lys-Gly-OH

Aβ 29-40
Ac-Lys-Gly-Ala-Ile-Ile-Gly-Leu-Met-Val-Gly-Gly-Val-Val-Lys-Gly-OH

FIGURE 5

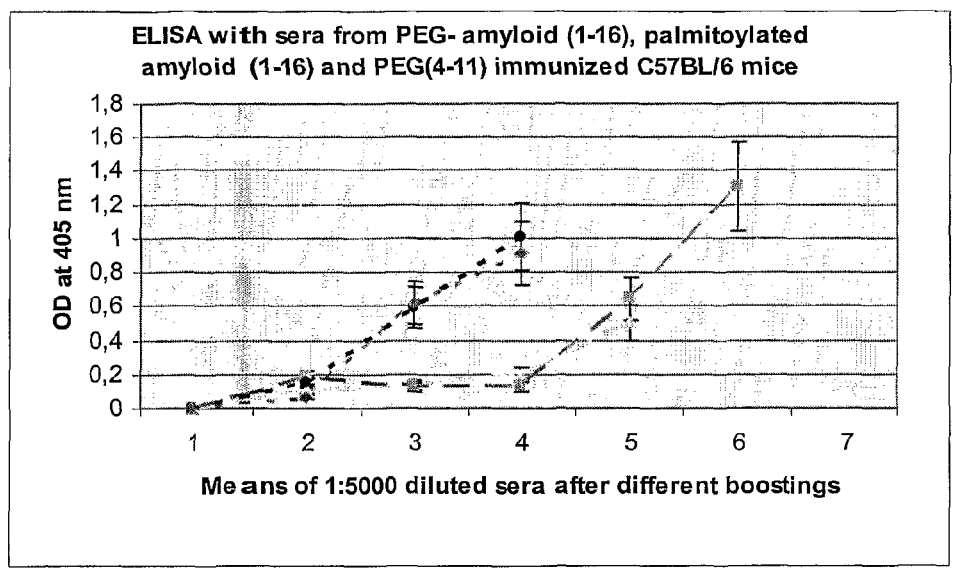

Figure 7: ELISA conducted with 1:5000 diluted sera from pegylated amyloid/ liposomes/ lipid A immunized C57BL/6 mice. PEG-A$\beta_{1-16}$ (- -black), PEG-A$\beta_{1-16}$ + ALUM (- -grey), PEG-A$\beta_{4-11}$ (————grey). Means of the values of 10 mice per antigen; means of values from 2 mice are shown for A$\beta_{1-16}$+ALUM. As a control mean values of 12 palmitoylated A$\beta_{1-16}$ (- - bright grey) injected animals are shown (published 2002).

|  | Amyloid β-peptide fibers | Amyloid β-peptide fibers after 12 days of incubation with the antibody |
|---|---|---|
| $^{12}$Val C$_\alpha$ | 58 ppm | 60 ppm |
| $^{12}$Val C$_\beta$ | 33 ppm | 30 ppm |
| $^{10}$Tyr C$_\alpha$ | 54 ppm | 56 ppm |
| $^{10}$Tyr C$_\beta$ | 38 ppm | 41 ppm |

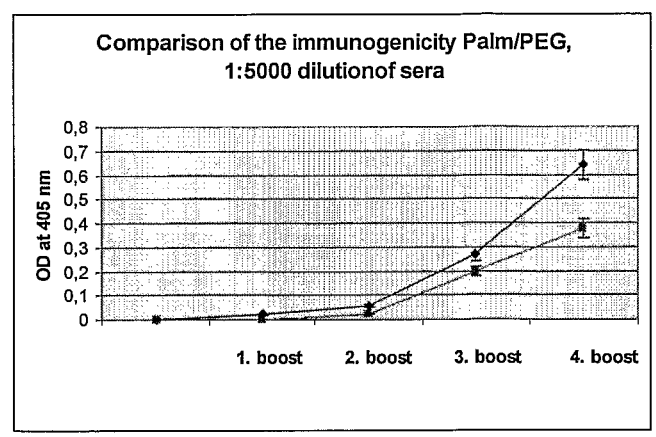
Figure 13: pink: Palm.-A$\beta_{1-16}$, blue: PEG-A$\beta_{1-16}$

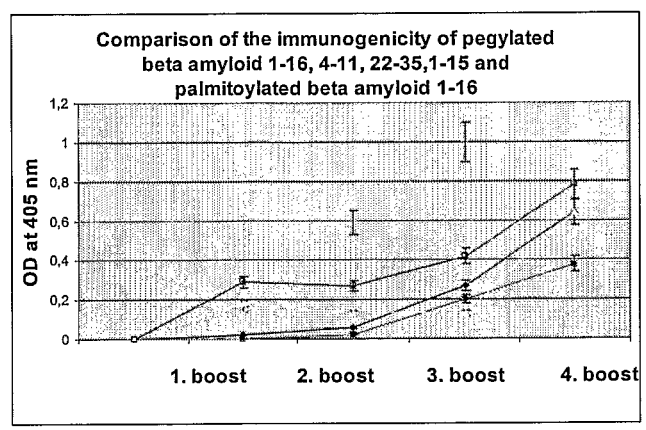
Figure 14: pink: Palm.-Aβ$_{1-16}$, blue: PEG-Aβ$_{1-16}$, turquoise: PEG-Aβ$_{1-15}$, violet: PEG-Aβ$_{22-35}$, yellow: PEG-Aβ$_{4-11}$.

SEQUENCE LISTING

<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: Synthetic constructs

<400> SEQUENCE: 1

Phe Arg His Asp Ser Gly Tyr
1               5

```
<210> SEQ ID NO 2
<211> LENGTH: 11
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (3)..(3)
<223> OTHER INFORMATION: Xaa = Arg(Pbf)
<220> FEATURE:
<221> NAME/KEY: MISC_FEATURE
<222> LOCATION: (4)..(4)
<223> OTHER INFORMATION: Xaa = His(Trt)
<220> FEATURE:
<221> NAME/KEY: MISC_FEATURE
<222> LOCATION: (5)..(5)
<223> OTHER INFORMATION: Xaa = Asp(OtBu)
<220> FEATURE:
<221> NAME/KEY: MISC_FEATURE
<222> LOCATION: (6)..(6)
<223> OTHER INFORMATION: Xaa = Ser(tBu)
<220> FEATURE:
<221> NAME/KEY: MISC_FEATURE
<222> LOCATION: (8)..(8)
<223> OTHER INFORMATION: Xaa = Tyr(tBu)
<220> FEATURE:
<221> NAME/KEY: MISC_FEATURE
<222> LOCATION: (9)..(9)
<223> OTHER INFORMATION: Xaa = Glu(OtBu)

<400> SEQUENCE: 2

Lys Phe Xaa Xaa Xaa Xaa Gly Xaa Xaa Lys Gly
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (2)..(2)
<223> OTHER INFORMATION: Xaa = Glu(OtBu)
<220> FEATURE:
<221> NAME/KEY: MISC_FEATURE
<222> LOCATION: (3)..(3)
<223> OTHER INFORMATION: Xaa = Asp(OtBu)
<220> FEATURE:
<221> NAME/KEY: MISC_FEATURE
<222> LOCATION: (6)..(6)
<223> OTHER INFORMATION: Xaa = Ser(tBu)
<220> FEATURE:
<221> NAME/KEY: MISC_FEATURE
<222> LOCATION: (7)..(7)
<223> OTHER INFORMATION: Xaa = Asn(Trt)
<220> FEATURE:
<221> NAME/KEY: MISC_FEATURE
<222> LOCATION: (8)..(8)
<223> OTHER INFORMATION: Xaa = Lys(Boc)

<400> SEQUENCE: 3

Lys Xaa Xaa Val Gly Xaa Xaa Xaa Gly Ala Ile Ile Gly Leu Met Lys
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: Synthetic constructs
```

<400> SEQUENCE: 4

Lys Gly Ala Ile Ile Gly Leu Met Val Gly Gly Val Val Lys Gly
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (2)..(2)
<223> OTHER INFORMATION: Xaa = Asp(OtBu)
<220> FEATURE:
<221> NAME/KEY: MISC_FEATURE
<222> LOCATION: (4)..(4)
<223> OTHER INFORMATION: Xaa = Glu(OtBu)
<220> FEATURE:
<221> NAME/KEY: MISC_FEATURE
<222> LOCATION: (6)..(6)
<223> OTHER INFORMATION: Xaa = Arg(Pbf)
<220> FEATURE:
<221> NAME/KEY: MISC_FEATURE
<222> LOCATION: (7)..(7)
<223> OTHER INFORMATION: Xaa = His(Trt)
<220> FEATURE:
<221> NAME/KEY: MISC_FEATURE
<222> LOCATION: (8)..(8)
<223> OTHER INFORMATION: Xaa = Asp(OtBu)
<220> FEATURE:
<221> NAME/KEY: MISC_FEATURE
<222> LOCATION: (9)..(9)
<223> OTHER INFORMATION: Xaa = Ser(tBu)
<220> FEATURE:
<221> NAME/KEY: MISC_FEATURE
<222> LOCATION: (11)..(11)
<223> OTHER INFORMATION: Xaa = Tyr(tBu)
<220> FEATURE:
<221> NAME/KEY: MISC_FEATURE
<222> LOCATION: (12)..(12)
<223> OTHER INFORMATION: Xaa = Glu(OtBu)
<220> FEATURE:
<221> NAME/KEY: MISC_FEATURE
<222> LOCATION: (14)..(14)
<223> OTHER INFORMATION: Xaa = His(Trt)
<220> FEATURE:
<221> NAME/KEY: MISC_FEATURE
<222> LOCATION: (15)..(15)
<223> OTHER INFORMATION: Xaa = His(Trt)
<220> FEATURE:
<221> NAME/KEY: MISC_FEATURE
<222> LOCATION: (16)..(16)
<223> OTHER INFORMATION: Xaa = Gln(Trt)
<220> FEATURE:
<221> NAME/KEY: MISC_FEATURE
<222> LOCATION: (17)..(17)
<223> OTHER INFORMATION: Xaa = Lys(Boc)

<400> SEQUENCE: 5

Lys Xaa Ala Xaa Phe Xaa Xaa Xaa Xaa Gly Xaa Xaa Val Xaa Xaa Xaa
1               5                   10                  15

Xaa Lys Gly

<210> SEQ ID NO 6
<211> LENGTH: 21
<212> TYPE: PRT
<213> ORGANISM: Artificial Sequence
<220> FEATURE:
<223> OTHER INFORMATION: Synthetic constructs -continued

```
<400> SEQUENCE: 6

Lys Thr Asn Met Lys His Met Ala Gly Ala Ala Ala Ala Gly Ala Val
1               5                   10                  15

Val Gly Gly Leu Gly
            20

<210> SEQ ID NO 7
<211> LENGTH: 8
<212> TYPE: PRT
<213> ORGANISM: Artificial Sequence
<220> FEATURE:
<223> OTHER INFORMATION: Synthetic constructs

<400> SEQUENCE: 7

Trp Gly Gln Pro His Gly Gly Gly
1               5

<210> SEQ ID NO 8
<211> LENGTH: 18
<212> TYPE: PRT
<213> ORGANISM: Artificial Sequence
<220> FEATURE:
<223> OTHER INFORMATION: Synthetic constructs

<400> SEQUENCE: 8

Trp Gly Gln Gly Gly Gly Thr His Ser Gln Trp Asn Lys Pro Ser Lys
1               5                   10                  15

Pro Lys

<210> SEQ ID NO 9
<211> LENGTH: 9
<212> TYPE: PRT
<213> ORGANISM: Artificial Sequence
<220> FEATURE:
<223> OTHER INFORMATION: Synthetic constructs

<400> SEQUENCE: 9

Lys Thr Asn Met Lys His Met Ala Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic constructs

<400> SEQUENCE: 10

Gly Tyr Met Leu Gly Ser Ala Met Ser
1               5

<210> SEQ ID NO 11
<211> LENGTH: 21
<212> TYPE: PRT
<213> ORGANISM: Artificial Sequence
<220> FEATURE:
<223> OTHER INFORMATION: Synthetic constructs

<400> SEQUENCE: 11

Gly Tyr Met Leu Gly Ser Ala Met Ser Arg Pro Ile Ile His Phe Gly
1               5                   10                  15

Ser Asp Tyr Glu Asp
            20
```

```
<210> SEQ ID NO 12
<211> LENGTH: 21
<212> TYPE: PRT
<213> ORGANISM: Artificial Sequence
<220> FEATURE:
<223> OTHER INFORMATION: Synthetic constructs

<400> SEQUENCE: 12

Asn Gly Ala Lys Ala Leu Met Gly Gly His Gly Ala Thr Lys Val Met
1               5                   10                  15

Val Gly Ala Ala Ala
            20
```

METHOD FOR IMPROVING MEMORY IN AD PATIENTS

CROSS-REFERENCE TO RELATED APPLICATIONS

The present application is a national stage application under 35 U.S.C. §371 of International Patent Application No. PCT/US2005/005285 filed Feb. 22, 2005, which is a continuation-in-part of to U.S. patent application Ser. No. 10/958,211 filed Oct. 4, 2004, now U.S. Pat. No. 8,663,650, which is a continuation-in-part of U.S. patent application Ser. No. 10/783,975 filed Feb. 20, 2014, now abandoned.

FIELD OF THE INVENTION

The present invention is related to methods and compositions for eliciting high immune responses. In particular, the present invention includes novel compositions and methods for yielding conformationally sensitive antibodies.

BACKGROUND OF THE INVENTION

The immune system is a complex response system of the body that involves many different kinds of cells that have differing activities. Activation of one portion of the immune system usually causes a variety of responses due to unwanted activation of other related portions of the system. Currently, there are no satisfactory methods or compositions for producing a specifically desired response by targeting the specific components of the immune system.

The immune system is a complex interactive system of the body that involves a wide variety of components, including cells, and cellular factors, which interact with stimuli from both inside the body and outside the body. Aside from its direct action, the immune system's response is also influenced by other systems of the body including the nervous, respiratory, circulatory, and digestive systems.

One of the better-known aspects of the immune system is its ability to respond to foreign antigens presented by invading organisms, cellular changes within the body, or from vaccination. Some of the first kinds of cells that respond to such activation of the immune system are phagocytes and natural killer cells. Phagocytes include among other cells, monocytes, macrophages, and polymorphonuclear neutrophils. These cells generally bind to the foreign antigen, internalize it and often times destroy it. They also produce soluble molecules that mediate other immune responses, such as inflammatory responses. Natural killer cells can recognize and destroy certain virally—infected embryonic and tumor cells. Other factors of the immune response include complement pathways, which are capable of responding independently to foreign antigens or acting in concert with cells or antibodies.

Generally, it is thought that the response to antigens involves both humoral responses and cellular responses. Humoral immune responses are mediated by non-cellular factors that are released by cells and which may or may not be found free in the plasma or intracellular fluids. A major component of a humoral response of the immune system is mediated by antibodies produced by B lymphocytes. Cell-mediated immune responses result from the interactions of cells, including antigen presenting cells and B lymphocytes (B cells) and T lymphocytes (T cells).

One of the most widely employed aspects of the immune response capabilities is the production of monoclonal antibodies. The advent of monoclonal antibody (Mab) technology in the mid 1970s provided a valuable new therapeutic and diagnostic tool. For the first time, researchers and clinicians had access to unlimited quantities of uniform antibodies capable of binding to a predetermined antigenic site and having various immunological effector functions. Currently, the techniques for production of monoclonal antibodies are well known in the art. However there remains a continuing need for specialized antibodies. In essence, what is desired is the ability to produce customized antibodies. The need is especially great in the area of combating infectious disease where pathogens have acquired resistance to commonly used antibiotics. In addition, there is a need for antibiotics, for addressing pathological conditions resulting from cause other than an infectious agent.

Alzheimer's Disease (AD) is a neurological disorder primarily thought to be caused by the build of amyloid plaques caused by abnormal deposit of proteins in the brain. Scientific evidence demonstrates that AD results from an increase in the production or accumulation of beta-amyloid protein in plaques that leads to nerve cell death. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). The degradation of APPs likely increases their propensity to aggregate in plaques. There is a need for specific antibodies that can target and diffuse amyloid plaque formation.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Mid-stage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests-such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), such as the cholinesterase inhibitors (ChEIs), have been shown to improve symptoms. Medications are also available to address the psychiatric manifestations of AD.

Cholinesterase inhibitors, such as Tacrine and Rivastgmine, are currently the only class of agents that are approved by the FDA for the treatment of AD. These agents are medicines that restore the defect, or malfunctioning, in the chemical neurotransmission in the brain. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress despite treatment, and the average effect on mental functioning has only been modest. ChEIs also have side effects that include gastrointestinal dysfunction, liver toxicity and weight loss.

Advances in the understanding of the brain abnormalities that occur in AD are hoped to provide the framework for new targets of treatment that are more focused on altering the course and development of the disease. Many compounds, including anti-inflammatory agents, are being actively investigated. Clinical trials using specific cyclooxygenase inhibitors (COX-2), such as rofecoxib and celecoxib, are also underway.

Another factor to consider when developing new drugs is the ease of use for the target patients. Oral drug delivery—specifically tablets, capsules and softgels—account for 70% of all dosage forms consumed because of patient convenience. Drug developers agree that patients prefer oral delivery rather than subjecting themselves to injections or other, more invasive forms of medicinal administration. Formulations resulting in low dosing intervals (i.e. once a day or sustained release) are also preferable. The ease of administering antibiotics in oral dosage forms results in an increase of patient compliance during treatment.

What is needed are effective methods and compositions for generation of highly specific and highly effective antibodies. Preferably such antibodies would recognize specific epitopes on various antigens such as amyloid protein, prion protein or $P_{170}$ glycoprotein.

What is also needed therefore, are effective compositions and methods for addressing the complications associated with neurological disease associated with amyloid plaque formation such as Alzheimer's disease. In particular what is need are specialized antibodies capable of counteracting the physiological manifestations of the disease such as the formation plaques associated with aggregation of fibers of the amyloid peptide in its beta sheet conformation.

SUMMARY OF THE INVENTION

The present invention includes novel methods and compositions for eliciting highly specific and highly effective antibodies. Unlike currently available products the present invention provides unique methods and compositions resulting in antibodies having the ability to recognize specific epitopes from a range of antigens.

The present invention satisfies the long felt need for compositions that enable the generation of antibodies that specifically recognize epitopes such as those of amyloid protein, prion protein or $P_{170}$ glycoprotein.

The present invention comprises unique antigen presentation that results in enhanced exposure and ultimately antibodies with a higher degree of conformational sensitivity. In one embodiment the invention includes compositions comprising supramolecular antigenic constructs comprising a peptide sequence, covalently attached to pegylated amino acid (such as pegylated lysine)—one at each terminus.

Accordingly, it is an object of the present invention to provide methods and compositions for eliciting specific and effective immune responses.

It is another object of the present invention to provide methods and compositions for treating and preventing the occurrence or spread of disease.

It is a further object of the present invention to provide methods and compositions for preventing, treating or reducing disease by eliciting an active cellular and humoral response in the host.

Yet another object of the present invention is to provide methods and compositions for reducing and preventing the occurrence of neurological disorders.

Another object of the present invention is to provide methods and compositions for reducing and preventing the occurrence of hyperproliferative disorders.

Yet another object of the present invention to provide methods and compositions for therapeutic immunological intervention in neurological disorders.

It is yet another object of the present invention to provide methods and compositions for vaccinating a human or animal against selected infectious organisms.

It is yet another object of the present invention to provide methods and compositions for passively immunizing a human or animal against selected infectious organisms.

Another object of the present invention is to provide supramolecular construct compositions that are antigenic and elicit an immune response against pathological manifestation in humans or animals.

Yet another object of the present invention is to provide supramolecular construct compositions that are antigenic and elicit an immune response against pathological manifestation in humans or animals, wherein such pathological manifestation comprises abnormalities such as amyloid plaques.

Another object of the present invention is to provide supramolecular construct compositions that are antigenic and elicit an immune response against infectious organisms in humans or animals.

Another object of the present invention is to provide vaccine compositions comprising supramolecular antigenic constructs that are non-immunogenic in a human or animal to be immunized with the composition; and carriers wherein the antigenic peptide is uniquely presented on the surface of the carrier such that resulting antibodies are highly specific and have a greater degree of conformational sensitivity when administered into the human or animal.

Yet another object of the present invention is to provide methods and compositions comprising modified antigenic moieties to increase an individual's response to disease and disorders.

Another object of the present invention is to provide vaccine compositions comprising supramolecular antigenic constructs wherein peptides are modified to enhance antigenic effect.

Yet another object of the present invention is to provide vaccine compositions comprising supramolecular antigenic constructs comprising peptides modified to enhance antigenic effect wherein such peptides are modified via pegylation (using polyethylene glycol or modified polyethylene glycol), or modified via other methods such by poly-amino acids (e.g. poly-glycine, poly-histidine), poly-saccharides (e.g. polygalacturonic acid, polylactic acid, polyglycolide, chitin, chitosan), synthetic polymers (polyamides, polyurethanes, polyesters) or co-polymers (poly(methacrylic acid) and N-(2-hydroxy)propyl methacrylamide) and the like.

It is yet another object of the present invention to provide immunogenic compositions wherein the carrier for the antigenic peptide comprises modified liposomes.

It is another object of the present invention to provide immunogenic compositions wherein the carrier for the antigenic peptide comprises a colloidal metal.

Another object of the present invention is to provide immunogenic compositions wherein the carrier for the antigenic peptide comprises a baculovirus-derived vesicle.

It is still another object of the present invention to provide immunogenic compositions in combination with pharmaceutically acceptable adjuvants to stimulate the immune response.

Yet another object of the present invention is to provide immunogenic compositions that may be administered intramuscularly, intravenously, transdermally, orally, or subcutaneously.

These and other objects, features and advantages of the present invention will become apparent after a review of the following detailed description of the disclosed embodiment and the appended claims.

BRIEF DESCRIPTION OF THE FIGURES

FIG. 2 provides representative schematic showing liposome reconstituted with a chemically modified amyloid-antigen.

FIG. 4 provides synthetic peptides, homologous to different segments of $PrP^c$ used to investigate their influence on the viability of primary rat hippocampal neurons. Letter "a" refers to SEQ ID NO: 7; letter "b" refers to SEQ ID NO: 8; letter "c" refers to SEQ ID NO: 9; letter "d" refers to SEQ ID NO: 6; letter "e" refers to SEQ ID NO: 10; letter "f" refers to SEQ ID NO: 11; and letter "g" refers to SEQ ID NO: 12.

FIG. 5 provides a schematic of the peptides derived from the Aβ sequences 4-11 (SEQ ID NO: 2), 1-16 (SEQ ID NO: 5), 22-35 (SEQ ID NO: 3) and 29-40 (SEQ ID NO: 4).

FIG. 7 provides the results of ELISA conducted with 1:5000 diluted sera from pegylated amyloid/liposomes/lipid A immunized C57BL/6 mice. PEG-A$β_{1-16}$ (- -black), PEG-A$β_{1-16}$+ALUM (- -grey), PEG-A$β_{4-11}$ (——grey). Means of the values of 10 mice per antigen; means of values from 2 mice are shown for A$β_{1-16}$+ALUM. As a control mean values of 12 palmitoylated A$β_{1-16}$ (- - bright grey) injected animals are shown (published 2002).

FIG. 13 provides a graph showing comparative data for pegylated and palmitoylated antigens.

FIG. 14 provides a graph showing comparative data for pegylated beta amyloid (1-16, 4-11, 22-35, 1-15) and palmitoylated beta amyloid (1-16).

DETAILED DESCRIPTION

Figure 1:
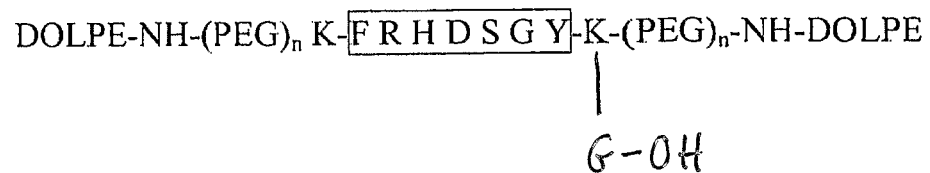
FIG. 1 provides a schematic showing chemically modified β-amyloid antigen.

The present invention may be understood more readily by reference to the following detailed description of specific embodiments included herein. Although the present invention has been described with reference to specific details of certain embodiments, thereof, it is not intended that such details should be regarded as limitations upon the scope of the invention. The text of the references mentioned herein are hereby incorporated by reference in their entirety, including U.S. Provisional Application Ser. No. 60/449,573, and U.S. patent application Ser. No. 10/783,975 filed Feb. 20, 2004.

We report here a method of eliciting high immune responses, of great specifity yielding conformationally sensitive antibodies. These antibodies recognize specific epitopes on a wide variety of antigens including but not limited to, amyloid protein, prion protein, $P_{170}$ glycoprotein. More specifically, we report here the concept of modifying peptides, such as amyloid peptides, to elicit an improved immunogenic response. In certain embodiments, the peptides are modified via pegylation.

Definitions

The terms "polypeptide", "peptide", and "protein", as used herein, are interchangeable and are defined to mean a biomolecule composed of two or more amino acids linked by a peptide bond.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" as used herein include monoclonal antibodies, polyclonal, chimeric, single chain, bispecific, simianized, and humanized antibodies as well as Fab fragments, including the products of an Fab immunoglobulin expression library.

The term "antigen" refers to an entity or fragment thereof which can induce an immune response in a mammal. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "carrier" as used herein means a structure in which antigenic peptide or supramolecular construct can be incorporated into or can be associated with, thereby presenting or exposing antigenic peptides or part of the peptide to the immune system of a human or animal. The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

In addition, the term "carrier" further comprises delivery mechanisms known to those skilled in the art including, but not limited to, keyhole limpet hemocyanin (KLH), bovine serum albumin (BSA) and other adjuvants. It is also to be understood that the supramolecular antigenic construct compositions of the present invention can further comprise adjuvants, preservatives, diluents, emulsifiers, stabilizers, and other components that are known and used in vaccines of the prior art. Any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Carrier proteins that can be used in the supramolecular antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "effective amount" refers to the amount of antigenic/immunogenic composition which, when administered to a human or animal, elicits an immune response. The effective amount is readily determined by one of skill in the art following routine procedures.

For example, supramolecular antigenic construct compositions may be administered parenterally or orally in a range of approximately 1.0 μg to 10.0 mg per patient, though this range is not intended to be limiting. The actual amount of the composition required to elicit an immune response will vary for each individual patient depending on the immunogenicity of the composition administered and on the immune response of the individual. Consequently, the specific amount administered to an individual will be determined by routine experimentation and based upon the training and experience of one skilled in the art.

The compositions of the present invention are used to produce antibodies directed against antigenic peptides. Resulting antibodies are administered to individuals to passively immunize them against a variety of diseases or disorders, including but not limited to, Alzheimer's disease, multidrug resistant cancer or prion disease.

The immunogenic compositions of the present invention may comprise liposomes made by reconstituting liposomes in the presence of purified or partially purified or modified antigenic peptides. Additionally, peptide fragments may be reconstituted into liposomes. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, nonionic block polymers, aluminum hydroxide or aluminum phosphate adjuvant, and mixtures thereof.

The present invention further encompasses antigenic peptides modified with hydrophobic moieties, such as palmitic acid, that facilitate insertion into the hydrophobic lipid bilayer of a carrier. Hydrophobic moieties of the present invention may be fatty acids, triglycerides and phospholipids wherein the fatty acid carbon back bones has at least 10 carbon atoms. Most preferable are lipophilic moieties having fatty acids with a carbon backbone of at least approximately 14 carbon atoms and up to approximately 24 carbon atoms. The most preferred hydrophobic moieties have a carbon backbone of at least 14 carbon atoms. Examples of hydrophobic moieties include, but are not limited to, palmitic acid, stearic acid, myristic acid, lauric acid, oleic acid, linoleic acid, and linolenic acid. The most preferred hydrophobic moiety is palmitic acid.

The supramolecular antigenic construct compositions of the present invention are administered to a human or animal to induce immunity to antigenic agents such as infectious organisms. The immunized human or animal develops circulating antibodies against the infectious organism, thereby reducing or inactivating its ability to stimulate disease.

The supramolecular antigenic construct compositions of the present invention are also used to produce a panel of monoclonal or polyclonal antibodies that are specific for various disorders, including for example, Alzheimer's disease. Antibodies are made by methods well known to those of ordinary skill in the art.

The compositions of the present invention are administered to a human or animal by any appropriate means, preferably by injection. For example, a modified antigenic peptide reconstituted in liposomes is administered by subcutaneous injection. Whether internally produced or provided from external sources, the circulating antibodies bind to antigen and reduce or inactivate its ability to stimulate disease.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., *Infect. Immun.* 60:2438-2444, 1992, hereby incorporated by reference. The liposome can optionally contain an adjuvant. A preferred adjuvant is detoxified lipid A, such as monophosphoryl or diphosphoryl lipid A.

When the vesicles are liposomes, the antigenic peptide generally has a hydrophobic tail that inserts into the liposome membrane as it is formed. Additionally, antigenic peptides can be modified to contain a hydrophobic tail so that it can be inserted into the liposome. For example, antigenic peptide may be exposed on the surface of previously formed liposomes by chemical attachment or electroinsertion.

The antibodies provided herein are monoclonal or polyclonal antibodies having binding specificity for infectious organisms or antigenic peptides representative of various disorders such as Alzheimer's disease, multi drug resistant cancer and prion diseases.

The monoclonal antibody is prepared by immunizing an animal, such as a mouse or rabbit, with supramolecular antigenic construct compositions of the present invention. Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against specific diseases or disorders. Hybridomas producing antibodies of interest are cloned, expanded and stored frozen for future production. The preferred hybridoma produces a monoclonal antibody having the IgG isotype, more preferably the IgG1 isotype.

The polyclonal antibody is prepared by immunizing animals, such as mice or rabbits with supramolecular antigenic construct compositions of the present invention described above. Blood sera is subsequently collected from the animals, and antibodies in the sera screened for binding reactivity against target agents.

Either the monoclonal antibody or the polyclonal antibody, or both may be labeled directly with a detectable label for identification a target agent in a biological sample as described below. Labels for use in immunoassays are generally known to those skilled in the art and include enzymes, radioisotopes, and fluorescent, luminescent and chromogenic substances including colored particles, such as colloidal gold and latex beads. The antibodies may also be bound to a solid phase to facilitate separation of antibody-antigen complexes from non-reacted components in an immunoassay. Exemplary solid phase substances include, but are not limited to, microtiter plates, test tubes, magnetic, plastic or glass beads and slides. Methods for coupling antibodies to solid phases are well known to those skilled in the art.

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

In a preferred embodiment, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

Formulations

The naturally occurring or synthetic protein, peptide, or protein fragment, containing all or an active portion of an immunogenic protein or peptide can be prepared in a physiologically acceptable formulation, such as in a pharmaceutically acceptable carrier, using known techniques. For example, the protein, peptide or protein fragment is combined with a pharmaceutically acceptable excipient to form a therapeutic composition.

Alternatively, the gene for the protein, peptide, or protein fragment, containing all or an active portion of the immunogenic peptide, may be delivered in a vector for continuous administration using gene therapy techniques. The vector may be administered in a vehicle having specificity for a target site, such as a tumor.

The compositions of the present invention may be administered in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The dosage of the composition will depend on the condition being treated, the particular composition used, and other clinical factors such as weight and condition of the patient, and the route of administration.

The composition may be administered in combination with other compositions and procedures for the treatment of diseases. For example, unwanted cell proliferation may be treated conventionally with surgery, radiation or chemotherapy in combination with the administration of the composition, and additional doses of the composition may be subsequently administered to the patient to stabilize and inhibit the growth of any residual unwanted cell proliferation.

Supramolecular Antigenic Constructs

The supramolecular antigenic constructs of the present invention generally comprise peptides modified to enhance antigenic effect wherein such peptides are modified via pegylation (using polyethylene glycol or modified polyethylene glycol), or modified via other methods such by palmitic acid, poly-amino acids (eg poly-glycine, poly-histidine), poly-saccharides (eg polygalacturonic acid, polylactic acid, polyglycolide, chitin, chitosan), synthetic polymers (polyamides, polyurethanes, polyesters) or co-polymers (eg. poly(methacrylic acid) and N-(2-hydroxy)propyl methacrylamide) and the like.

In certain embodiments, the supramolecular antigenic constructs of the present invention comprise a peptide sequence, covalently attached to pegylated lysine—one at each terminus. The length of the PEG (polyethylenglycol) chain may vary from 8 to 150000. The free PEG terminus is covalently attached to a molecule of phosphatidylethanolamine (where the fatty acid can be: myristic, palmitic, stearic, oleic etc. or combination thereof). This supramolecular structure may be reconstituted in liposomes consisting of phospholipids and cholesterol (phosphatidylethanol amine, phosphatidyl glycerol, cholesterol in varied molar ratios. Other phospholipids can be used. Lipid A is used at a concentration of approximately 40 μg/pmole of phospholipids.

In certain embodiments, the supramolecular antigenic constructs comprise a peptide having the amino acid sequence of f3-amyloid. The peptides may also comprise or correspond to whole amyloid beta peptide and active fragments thereof. Additionally, peptides useful for the present invention further comprise $A\beta_{4-11}$ (SEQ ID NO: 2), $A\beta_{22-35}$ (SEQ ID NO: 3), and $A\beta_{29-40}$ (SEQ ID NO: 4) and $A\beta_{1-16}$ (SEQ ID NO: 5); and active fragments thereof.

In certain other embodiments, the supramolecular 1 antigenic construct comprises peptide sequences that comprise the extracellular loops 1, 4 and 6 of the P170 glycoprotein. In certain other embodiments, the supramolecular 1 antigenic construct comprises peptide sequences that comprise amino acid sequences 109-129 of the prion protein.

The present invention further comprises monoclonal antibodies raised against a supramolecular structure reconstituted in liposome, wherein, for example, the peptide sequence comprises an amino acid sequence from amyloid protein. Additionally, monoclonal antibodies raised against supramolecular structures wherein the peptide sequence is an/or several amino acid sequences from the P-glycoprotein ($P_{170}$) extracellular loops are also included in the present invention.

Also included in the present invention are monoclonal antibodies raised against a supramolecular structure wherein the peptide sequences comprise an amino acid sequence selected from a protein of interest. More specifically, for example, the invention includes monoclonal antibodies raised against a supramolecular structure reconstituted in liposome wherein the peptide sequence is an amino acid sequence selected from 13-amyloid protein (4-10, or 1-8, or 8-16, etc.) which does not induce cerebral bleeding in transgenic mice for human Alzheimer's disease. The invention further includes monoclonal antibodies sensitive to the conformational characteristics of antigenic peptides. Specific protocols for the manufacture of the antibodies of the present invention and specific information regarding the characterization of such antibodies are provided in the Examples below.

Amyloid

The 7 amino acid sequence: FRHDSGY (SEQ ID NO:1) of β-amyloid was synthesized. One lysine was attached covalently at each end of the sequence (1). The lysines, prior to attachment to the above sequence were reacted with a chain of Polyethylenglycol (PEG, n=8-2000). Polyethylenglycol chains bound to lysine at one end are covalently attached to a molecule of dioleyl-phosphatidyl choline ethanolamine (or any fatty acid-phosphatidylcholine) as described (2).

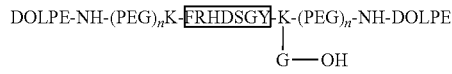

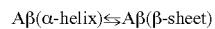

Chemically Modified β-amyloid Antigen

The chemically modified antigen is then reconstituted in liposomes consisting of phospholipids and cholesterol (3). Examples of suitable liposomes include, but are not limited to, DOPG, DOPEA, Chol. (Lipid A was at the concentration of 40 μg/μmole phospholipid.) A representative schematic showing liposome reconstituted with a chemically modified amyloid-antigen is shown in FIG. 2.

The supramolecular antigenic constructs of the present invention have vast advantages over the palmitoylated antigens, reconstituted in liposomes. Primarily, the long PEG chains (n=8-5000) enhance significantly the exposure and accessibility of the peptide sequence. Antigen presentation is improved and the conformation sensitivity of the elicited antibodies is enhanced. Another advantage of the present invention is that peptide sequences in different conformations may be used. The increased distance between the sequence and surface of the liposome makes sure that the surface does not interact with the sequence, thus, possibly influencing its conformation. Also, antigenicity of the construct becomes significantly higher than that of palmitoylated sequences reconstituted in liposomes. High titers of antibodies comprised between 1:5000 and 1:10000 are obtained in mice, within a few weeks. Additionally, the affinity of the antibodies for the antigen is significantly increased. In the case of the amyloid sequence FRHDSGY (SEQ ID NO:1), the antibody elicited by ip or iv injection of the construct are efficiently solubilizing $A\beta_{1-40}$ and $A\beta_{1-42}$ fibers, protecting in vitro PC12 cells against apoptosis and metabolic inhibition (MTT reduction) induced by $A\beta_{1-42}$ and $A\beta_{1-40}$ fibers.

In one embodiment of the present invention, the FRHDSGY (SEQ ID NO: 1) sequence of the amyloid protein is used, however any other amyloid protein sequence can be substituted. Monoclonal antibodies obtained from mice immunized with the described construct display, besides the in vitro properties mentioned above for the polyclonal antibodies, biological activity in APP[V7171] FVB transgenic mice for human Alzheimer's Disease. Significant levels of memory restoration and of curiosity awakening in these mice are observed. The mAb does not induce bleeding in the brain of the immunized, transgenic mice.

Though not wishing to be bound by the following theory, based on in vitro studies of the interaction of anti-amyloid mAb (against the 1-16 sequence, generated by the methods of the present invention) mainly of fiber solubilization and of CD spectra, it appears that the antibodies bind preferentially to β-amyloid in its α-helix conformation. This would explain the amyloid fiber solubilization effect in thermodynamic terms. Since the antibody, by binding preferentially to the α-helix, removes the α-helix amyloid from the equilibrium:

$$A\beta(\alpha\text{-helix}) \leftrightharpoons A\beta(\beta\text{-sheet})$$

thereby increasing amounts of β-amyloid, in β-sheet conformation undergo conformational transition to the soluble α-helix form in order to re-establish the equilibrium. The stochiometric observations made, support the idea of the mAbs directly influencing the conformation equilibrium.

As Selkoe (2002) has elaborated, Alzheimer's Disease appears as a synaptic failure. In the earlier stages of the disease memory loss may originate in such failure. It is thought that soluble oligomers $A\beta_{1-40}$, for example, might be able to block the synapse. The monoclonal antibodies, generated by methods of the present invention, bind to soluble oligomers $A\beta_{1-40}$. Measurement of conductivity of synapses in the presence and absence of the antibodies permits the determination of the action of the antibody on synapses, in the presence of soluble oligomers.

The inventors of the present invention checked the activity of a number of mAbs obtained with the epitopes such as $A\beta_{4-11}$ (SEQ ID NO: 2), $A\beta_{22-35}$ (SEQ ID NO: 3), and $A\beta_{29-40}$ (SEQ ID NO: 4) embedded in an supramolecular construct (see FIG. 5). The sequence 4-11 was determined to be the epitope to the mAb elicited by the palmitoylated Aβ 1-16 antigen (SEQ ID NO: 5).

According to the methods of the present invention, new and uniquely modified peptide antigens were used in order to raise mAbs:

```
Residue 22-35:   EDVGSNKGAIIGLM   (SEQ ID NO: 3)
```

Junctions between extracellular and transmembrane (TM) domains have been found to be targeted by inhibitory antibodies (such as Herceptin-Trastuzumab anti-HER2/neu antibodies) and, in multispanning TM proteins, to form pockets that are targeted by small molecular weight inhibitors (Dragic et al., 2000). Though not wishing to be bound by the following theory, this sequence is likely to be crucial for the oligomerization capacity of $A\beta_{1-42}$ and $A\beta_{1-40}$, as it represents the transition between polar and hydrophobic regions (wherein the phrase "extracellular sequence" is used to refer to the extracellular sequences in the $A\beta_{1-42}$ amyloidogenic sequence). The sequence contains the first two GXXXGXXXG motifs of the $A\beta_{1-42}$ and $A\beta_{1-40}$ sequences. GXXXG are key inducers of oligomerization of hydrophobic sequences (Russ and Engelmann, 2000). Interestingly, the first GXXXG motif is predicted to be extracellular, while the following two are predicted to be placed in the membrane. Though not wishing to be bound by the following theory, it may be assumed, by analogy, that oligomerization of $A\beta$ peptides is specifically triggered by the GXXXG motifs.

```
Residue 29-40:   GAIIGLMVGGVV     (SEQ ID NO: 4)
```

The hydrophobic sequence of $A\beta_{1-42}$ and $A\beta_{1-40}$ contain the motif GXXXGXXXGG, which has been found to induce strong oligomerization of hydrophobic sequences (Eilers et al., 2002; Leeds et al., 2001; Lemmon et al., 1994; Russ and Engelmann, 1999; Russ and Engelmann, 2000; Smith and Bormann, 1995). This motif is viewed as a prime target for therapeutic approaches; since it must play a major role in all pathogenic processes that lead to $A\beta_{1-42}$ and $A\beta_{1-40}$ formation, oligomerization and accumulation. In the intact sequence of APP, it is likely that this motif caps the downstream sequence that will need to unfold for γ-secretase to process, as was shown for the SREBP cleavage (Ye et al., 2000). This sequence has not previously been identified by anybody as being important for amyloid oligomerization. As taught herein, the supramolecular modified (preferably pegylated) antigens of the present invention have higher antigenicity and the antibodies elicited by them have higher affinities. Beside $A\beta_{1-16}$, supramolecular constructs of the present invention also include peptides represented by $A\beta_{4-11}$ (SEQ ID NO: 2), $A\beta_{22-35}$ (SEQ ID NO: 3), $A\beta_{29-40}$ (SEQ ID NO: 4) for use in vaccines.

Methodologies for the mono-pegylation of peptides at the N-α-position are known and widely used. Site-specific mono-pegylation at internal, N- or C-terminal amino-acid residues of medium sized peptides has also been described following either solid-phase or peptide-grafting approaches. However, solid-phase synthetic approaches to di-pegylated peptides have been shown to be severely hampered by steric hindrance and upon starting this project no efficient synthetic methodologies were reported for such compounds. Furthermore, peptides derivatised site-specifically at the N- and C-termini with both a PEG and lipid moiety have not previously been reported. Herein the present inventors describe a novel methodology for the synthesis of such $A\beta$ peptide conjugates.

In arriving at the present invention several approaches were attempted most of which were unsuccessful. For example, the initial approach to the synthesis focused upon the on-resin grafting of lipid-PEG conjugates containing distal amine groups, to side-chain protected peptides ($A\beta_{4-11,\ 1-16,\ 22-35}$ and $_{29-40}$) containing terminal Glutamic acid residues. No coupling products were observed under a wide variety of reaction conditions. As described in Example 2 and shown in FIG. 5, the supramolecular constructs described herein were generally synthesized using Fmoc/tBu amino acid side-chain protections.

This novel approach to the synthesis of N- and C-terminal lipid-PEG β-amyloid antigens using protected peptides is applicable to a wide variety of peptide sequences including for example multi-drug resistance protein P-glycoprotein.

In an effort to evaluate the efficacy of the antigenic peptides described herein, experiments were conducted to compare the immunogenicity of PEGylated and palmitoylated antigens using ELISA and disaggregation assays (see Example B, and FIG. 7). The ELISA data showed that liposomal PEG-$A\beta_{1-16}$ is significantly more immunogenic than palmitoylated $A\beta_{1-16}$. Additional ALUM did not enhance the immunogenicity of PEG-$A\beta_{1-16}$ in the mice. The antibody response induced by PEG-$A\beta_{4-11}$ was slower in comparison to PEG-$A\beta_{1-16}$.

In summary therefore, present invention provides novel monoclonal antibodies against supramolecular antigens exposing different amyloid sequences. In particular, original synthetic pathways were devised in order to bind covalently two polyethylene glycol (n=70) chains to selected amyloid sequences. At the free end of the PEG chain, phosphatidyl ethanol amine was covalently attached. Though not wishing to be bound by the following theory, it is believed that its function is to anchor the pegylated amyloid sequence in the bilayer of liposomes. Pegylation is shown herein to increase the immunogenicity of the antigens as compared to palmitoylation. Affinity studies, epitope determination, induction of conformational transition by these monoclonal antibodies are being conducted presently in our laboratory. The unique modification methodology of the present invention is applicable to a variety of peptides and can ultimately be employed in therapeutic formulations and vaccines for diseases and disorders including, but not limited to Alzheimer's disease, cancer, and infectious disease.

As described herein, the supramolecular antigenic constructs of the present invention comprise peptides modified to enhance antigenic effect wherein such peptides are modified via pegylation (using polyethylene glycol or modified polyethylene glycol), or modified via other methods such by palmitic acid, poly-amino acids (e.g. poly-glycine, poly-histidine)poly-saccharides (e.g. polygalacturonic acid, polylactic acid, polyglycolide, chitin, chitosan), synthetic polymers (polyamides, polyurethanes, polyesters) or co-polymers (poly(methacrylic acid) and N-(2-hydroxy)propyl methacrylamide) and the like. For therapeutic intervention in neurological disorders such as Alzheimer's disease, the present invention comprises the modification of amyloid beta peptides.

Multidrug Resistance 1 (MDR 1) in Cancer Cells

Multidrug resistance 1 in cancer cells is caused by the overexpression of the P-glycoprotein ($P_{170}$), a membrane pump which ejects a large variety of unrelated chemotherapy agents from cancer cells.

Immunization with palmitoylated extracellular sequences of $P_{170}$, reconstituted in liposomes, led to restoration of the sensitive phenotype in vitro in MDR1 $L_{1210}$ mouse leukemia cells (3). Further results have been obtained in vivo (Madoulet, Tosi, Nicolau et al., 2002—unpublished results) indicating a 70% increase of survival half-life in immunized mice, inoculated with MDR cancer cells, undergoing chemotherapy.

The inventors of the present invention demonstrate herein that an antigen consisting of the $P_{170}$ extracellular sequences 1,4 and 6 constructed, according to the method of the present invention is far more efficient in eliciting antibodies which largely revert the MDR phenotype to the sensitive phenotype in vitro and in vivo.

According to the methods of the present invention, peptides corresponding to $P_{170}$ extracellular loops 1, 4 and 6 were synthesized and then attached to pegylated lysines—1 at each end—which in turn were covalently attached to one dioleyl phosphatylethanolamine molecule at each end. Any fatty acid, myristic, palmitic, stearic or polyunsaturated fatty acids may be used.

These 3 constructs were reconstituted in liposomes consisting of PC-PEA-PG-Cholesterol (or any other phospholipid and cholesterol combination). Lipid A was added at concentration of 40 µg/µmole of phospholipids. The ratio peptide: phospholipid was 1:200 (other ratios may be used).

Figure 3:
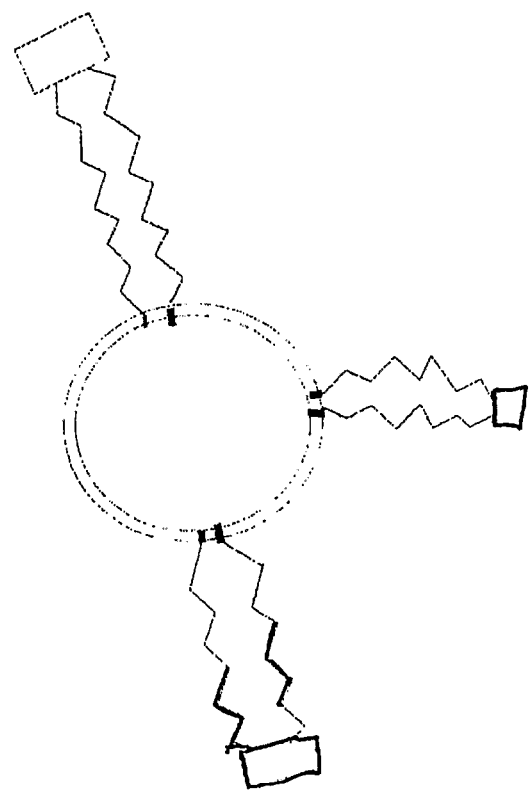
FIG. 3 provides a schematic showing a multiple $P_{170}$ antigen.

The length of the polyethylenglycol chains varied: the longer the peptide sequence, the higher the number of PEG molecules in the chain needs to be. For the 3 sequences used, the PEG chain-length varied from 10 to 5000. Other chain lengths can be used. FIG. 3 provides a representative schematic showing a multiple $P_{170}$ antigen.

IP inoculation of this antigen, followed by three boostings at 2 weeks interval elicited high titres of anti $P_{170}$ antibodies (1:5000-1:10000) capable of blocking the pumping activity of $P_{170}$, in vitro and in vivo.

Prion Diseases

Prions cause neurodegenerative diseases such as scrapie in sheep, bovine spongiform encephalopathy in cattle and Creutzfeldt-Jacob-Disease in humans. The only known component of the particle is the scrapie isoform of the protein, $PrP^{Sc}$. Although prions multiply, there is no evidence that they contain nucleic acid. $PrP^{Sc}$ is derived from the non-infectious, cellular protein $PrP^c$ by a posttranslational process during which $PrP^c$ undergoes a profound conformational change.

The scrapie protein, $PrP^{Sc}$ has a critical role in neuronal degeneration and during disease development undergoes a three stage transition as follows: (normal cellular isoform of protein) $PrP^c$-infectious form (scrapie isoform of protein) $PrP^{Sc}$-protein PrP27-30. Such a cascade of events occurs during the development of Creutzfeldt-Jacob Disease (CJD), Kuru, Gerstmann-Straussler-Scheinker Syndrome (GSS), fatal familial insomnia in man, scrapie in sheep and goats, encephalopathy in mink and bovine spongiform encephalopathy in cattle.

The cellular non-toxic protein ($PrP^c$ is a sialoglycoprotein of MW 33-35 K that is expressed predominantly in neurons. In the diseases mentioned above, $PrP^c$ is converted into an altered form ($PrP^{Sc}$), which is distinguishable from its normal homologue by its relative resistance to protease digestion. $PrP^{Sc}$ accumulates in the central nervous system of affected animals and individuals and its protease-resistant core aggregates extracellularly. The molecular basis of the pathogenesis is not understood.

Very interesting observations were made concerning the neurotoxicity of a fragment of the protein, which may have a bearing on the understanding of the mechanism of nerve cell-degeneration occurring in related encephalopaties.

On the basis of the observation, that the (J-amyloid fragment responsible for the extracellular deposition of amyloid fibrils and plaques in the Alzheimer Disease is neurotoxic, it was hypothesized that neuronal death in related encephalopathies might be due to toxic effects of abnormal extracellular accumulation of $PrP^{Sc}$ and/or its degradation products.

Synthetic peptides, homologous to different segments of $PrP^c$ were used to investigate their influence on the viability of primary rat hippocampal neurons (FIG. 4)

The present inventors demonstrated that neuronal death occurs from chronic exposure of primary rat hippocampal cultures to micromolar concentrations of a peptide corresponding to residues 106-126 of the amino-acid sequence deduced from human $PrP^c$ cDNA, in a concentration dependent manner (Example 1).

As detailed in Example 1, the inventors showed that the neuronal death induced by PrP 106-126 occurred by apoptosis in a dose dependent manner. In the terminal stages of subacute encephalopaties, such as scrapie, $PrP^{Sc}$ reaches at whole brain concentrations 10 to 20 times higher than $PrP^c$, which resembles strikingly the data listed in Table 1 for the 2 concentrations of PrP106-126.

The process of programmed cell death induced by PrP106-126 is associated, among others with the induction of the testosterone-repressed prostate message-2 gene (TRPM-2). It is not known whether apoptosis is activated in vivo during-related encephalopaties, but the expression of the TRPM-2 mRNA is increased 10-fold in scrapie-infected hamsters.

It appears from these data, that a neurotoxic mechanism is possibly responsible for neuronal cell loss in related encephalopaties and could also be relevant in Alzheimer's disease.

The possible mechanism of this neurotoxicity was investigated in a model system aiming at detecting and analyzing ionic channel formations upon the interaction of peptides or proteins with lipid bilayers.

Low pH, which favors channel formation by PrP106-126, converts also this peptide from ahelical to R-sheet conformation. Whereas peptide mapping of $PrP^{Sc}$ with Edman sequencing and mass spectrometry revealed no differences between its amino acid sequence and that predicted from the $PrP^c$ gene sequence; no chemical modifications where found that might distinguish $PrP^{Sc}$ from $PrP^p$; Fourier Transform infrared spectroscopy and circular dichroism spectroscopy revealed however a significant conformational difference between $PrP^{Sc}$ and $PrP^p$.

$PrP^c$ is essentially α-helical with little or no R-sheet, whereas $PrP^{Sc}$ has a high β-sheet content and less α-helical structure.

The sequence KTNMKHMAGAAAAGAVVGGLG (PrP106-126) (SEQ ID NO: 6) is not only very hydrophobic but it converts also, at low pH to β-sheet conformation. Moreover, it can convert in solution, other peptides to β-sheet conformation.

Based upon these observations and upon techniques developed by the inventors, a "vaccine" was developed against diseases by eliciting a strong humoral and cellular immune response in mice to the neurotoxic PrP106-126, and then challenge the immunized mice with brain extracts from scrapie mice.

As in the previous examples, pegylated lysines were attached covalently at each end of the PrP106-126 sequence. The length of the PEG chain was 12-4000. The PEG chains were coupled each other to one molecule of phosphatidyl ethanol amine and reconstituted in PG-PEA-chol liposomes-lipid A.

Injected into mice these supramolecular antigenic constracts elicited a strong humoral immune response, yielding antibodies with high affinity for the PrP106-126 sequence, and having solubilizing effects within.

It should be understood that the foregoing relates only to preferred embodiments of the present invention, and that numerous modifications or alterations may be made therein without departing from the spirit and the scope of the invention as set forth in the appended claims. The references cited throughout are hereby incorporated by reference in their entireties.

EXAMPLE 1

The present inventors demonstrated that neuronal death occurs from chronic exposure of primary rat hippocampal cultures to micromolar concentrations of a peptide corresponding to residues 106-126 of the amino-acid sequence deduced from human $PrP^c$ cDNA, in a concentration dependent manner. The data are shown in Table 1.

TABLE 1

Chronic treatment of hippocampal neurons for 9 days

| Peptide | cell death % | |
|---|---|---|
| | 20 μm | 80 μm |
| PrP 106-126 | 18 ± 8 | 100 ± 8 |
| PrP 57-64 | 0 ± 5 | 3 ± 4 |
| PrP 89-106 | 5 ± 2 | 2 ± 6 |
| PrP 106-114 | 0 ± 3 | 12 ± 6 |
| PrP 127-135 | 3 ± 6 | 15 ± 9 |
| PrP 127-147 | 1 ± 7 | 18 ± 7 |
| PrP 106-126 scrambled | 3 ± 2 | 8 ± 3 |

The data are the means±s.e. of 6-10 determinations and are normalized to the toxic effect of PrP106-126 (designated 100% response).

It was shown that the neuronal death induced by PrP 106-126 occurred by apoptosis in a dose dependent manner. In the terminal stages of subacute encephalopaties, such as scrapie, $PrP^{Sc}$ reaches at whole brain concentrations 10 to 20 times higher than $PrP^c$, which resembles strikingly the data listed in Table 1 for the 2 concentrations of PrP106-126.

The process of programmed cell death induced by PrP106-126 is associated, among others with the induction of the testosterone—repressed prostate message—2 gene (TRPM-2). It is not known whether apoptosis is activated in vivo during-related encephalopaties, but the expression of the TRPM-2 mRNA is increased 10-fold in scrapie-infected hamsters.

EXAMPLE 2

Methods for Making Supramolecular Antigenic Constructs

The supramolecular constructs described herein were uniquely synthesized using standard Fmoc/tBu amino acid side-chain protections. Peptides which are modified at both the C- and N-terminus by a PEG-lipid moiety have not previously been reported. Typically, pegylation of peptides results in mixtures of regioisomers. The inventors herein demonstrate a convenient method for the site-specific attachment of a PEG-lipid conjugate to both the C- and N-terminus of Aβ using partially protected peptides.

For those peptide sequences containing internal Lys or His residues (4-11, 1-16, 22-35), an orthogonally protected Lys (ivDde) was added to each termini. An additional Gly was added to the C-terminal to facilitate synthesis. The Fmoc group was removed with 20% piperidine in DMF and N-acetylated using acetic anhydride. Selective cleavage of the ivDde groups was achieved with 3% hydrazine hydrate in DMF for one hour. The 2-chlorotrityl resin was favored over the more widely used Wang resin since the former proved to be much more resistant to hydrazinolysis. Furthermore, the 2-chlorotrityl resin is extremely acid sensitive and thus, unlike the Wang resin, enables the isolation of protected peptides. Indeed, it was necessary to perform the coupling reaction in the solution phase as coupling of the resin-bound peptide to the pre-activated pegylated lipid reagent DSPE-PEG-SPA did not give rise to any coupling product. Thus selective cleavage from the resin under mild conditions (acetic acid/trifluoroethanol/dichloromethane, 1:1:8, 1 h, rt) gave the internally protected peptides (FIG. 5).

Figure 6:
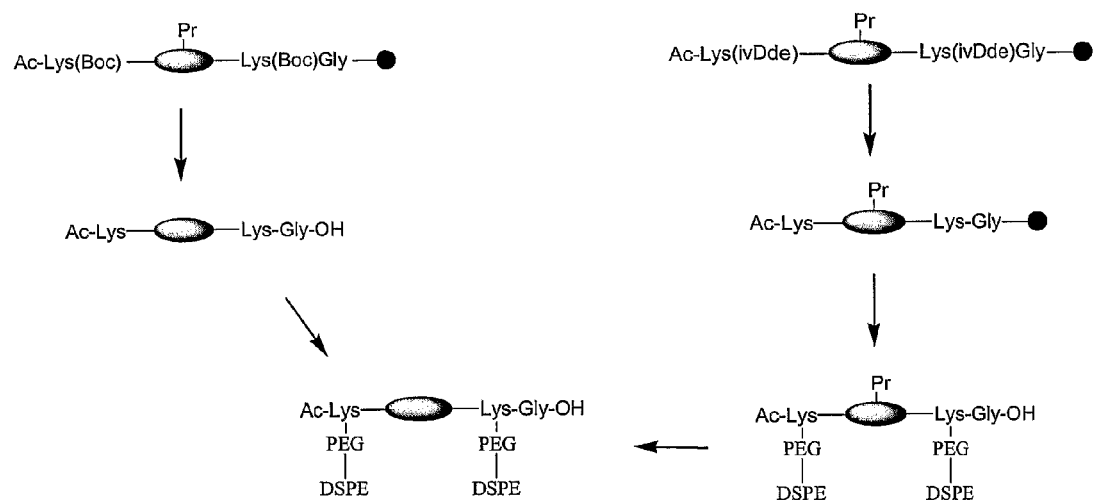
FIG. 6 provides a schematic showing the general synthetic approaches to antigens derived from peptides sequences with or without internal His or Lys residues.

Solution-phase couplings were achieved successfully with the peptides derived from sequences $Aβ_{4-11}$ (SEQ ID NO: 2), $Aβ_{1-16}$ (SEQ ID NO: 5), $Aβ_{22-35}$ (SEQ ID NO: 3), to DSPE-PEG-SPA in DMSO and excess base (FIG. 6). The reactions were then quenched by the addition of excess ethanolamine for 2 h and the solution lyophilized. Purification by HPLC (semi-preparative reverse-phase $C_4$ column) gave between 50-70% purity of the N- and C-terminal PEG-lipid conjugates whose identities were confirmed by MALDI (matrix assisted laser desorption ionization). Each sequence showed considerable variation in the ease of the coupling reaction and conditions were adjusted accordingly (temperature, number of molar equivalents DSPE-PEG-SPA, time). Purification by HPLC proved excellent for the separation of excess DSPE-PEG-SPA from the desired product, however since the former shows no affinity to the column, separation of mono-PEG-lipid (both N- and C-terminal) peptide products from the desired product proved difficult. Attempts to separate these products using size-exclusion chromatography also proved unsuccessful, presumably due to their relatively large polydispersities. Nevertheless the present inventors are using cation-exchange chromotagraphy to separate the mono- and di-coupled products before final side-chain deprotections. Subsequent peptide side-chain deprotections and separation of the excess quenched DSPE-PEG-SPA enables the isolation of the desired conjugates to much higher purity.

EXAMPLE 3

Comparison of Immunogenicity of PEGylated and Palmitoylated Antigens, ELISA and Disaggregation Assays Liposomal antigens were prepared as described above. The sequences PEG-$Aβ_{1-16}$, -$Aβ_{4-11}$ and -$Aβ_{22-35}$ were reconstituted in a construct consisting of liposomes made of dimyristoyl phosphatidyl choline (DMPC), dimyristoyl phosphatidyl ethanolamine (DMPEA), dimyristoyl phosphatidyl glycerol (DMPG) and cholesterol (0.9: 0.1: 0.1: 0.7 molar ratios) containing monophosphoryl lipid A (40 mg/mM phospholipids).

ELISA

The antigens and palmitoylated $Aβ_{1-16}$ were used for the immunization in C57BL/6 mice in 2 week intervals. 10-12 animals were immunized with each antigen. Sera were taken 5 days after the boostings and ELISA were conducted with several dilutions of the sera. Comparative results showing the immunogenicity of the different antigens are presented in FIG. 7.

The ELISA data showed that liposomal PEG-$Aβ_{1-16}$ is significantly more immunogenic than palmitoylated $A62_{1-16}$. Additional ALUM did not enhance the immunogenicity of PEG-$Aβ_{1-16}$ in the mice. The antibody response induced by PEG-$Aβ_{4-11}$ was slower in comparison to PEG-$Aβ_{1-16}$.

Disaggregation Assays

Nine sera (1:100 dilution) from the liposomal-PEG-Aβ$_{4-11}$ immunized animals were used in an assay where pre-formed Aβ$_{1-42}$ fibers were incubated with the antisera. The assay was performed as described (Nicolau et al., 2002).

Figure 8:
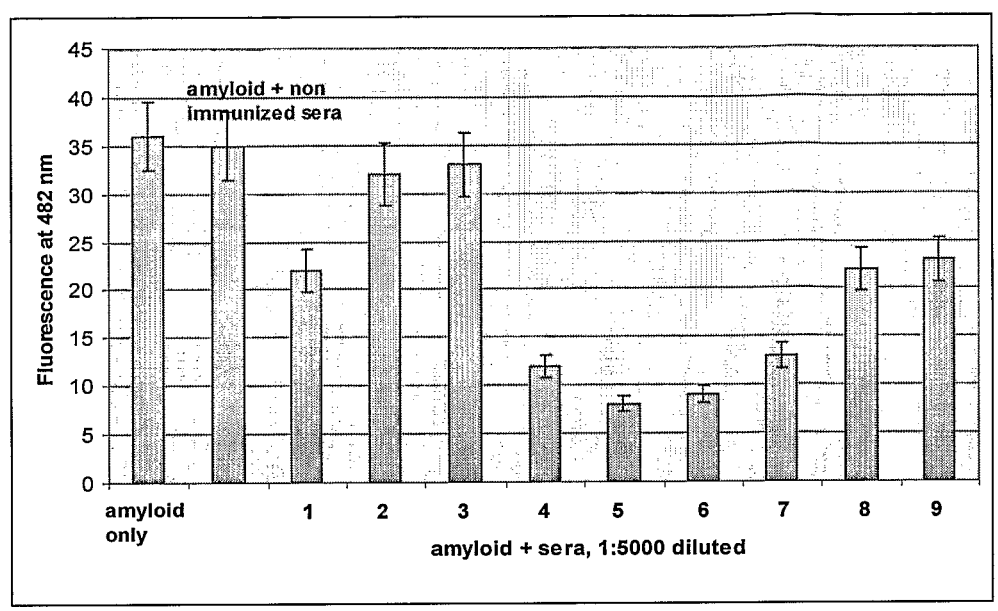
FIG. 8 provides the results of assays evaluating solubilization of A$β_{1-42}$ fibers by sera of PEG-A$β_{4-11}$ immunized C57BL/6 mice. Thioflavin fluorescence emission intensity correlates with the amount of fibrillar amyloid present in solution. A$β_{1-42}$ fibers formation during 7 days at 37° C. in PBS, pH=7.1. Sera were added on day 7 and incubated for 24 hrs. Bars 1-9 represent solubilization experiments made with sera of vaccinated animals. Means of 4 samples+SD are shown.

Solubilization of Aβ$_{1-42}$ fibers by the different sera was observed with an incubation time of 24 hrs (FIG. 8) Some of the sera solubilized the fibers to an extent of 75% (sera from mouse 5 and 6). The spleen cells of these mice were used for the production of monoclonal antibodies.

EXAMPLE 4

Solubilization Assay

Figure 9:
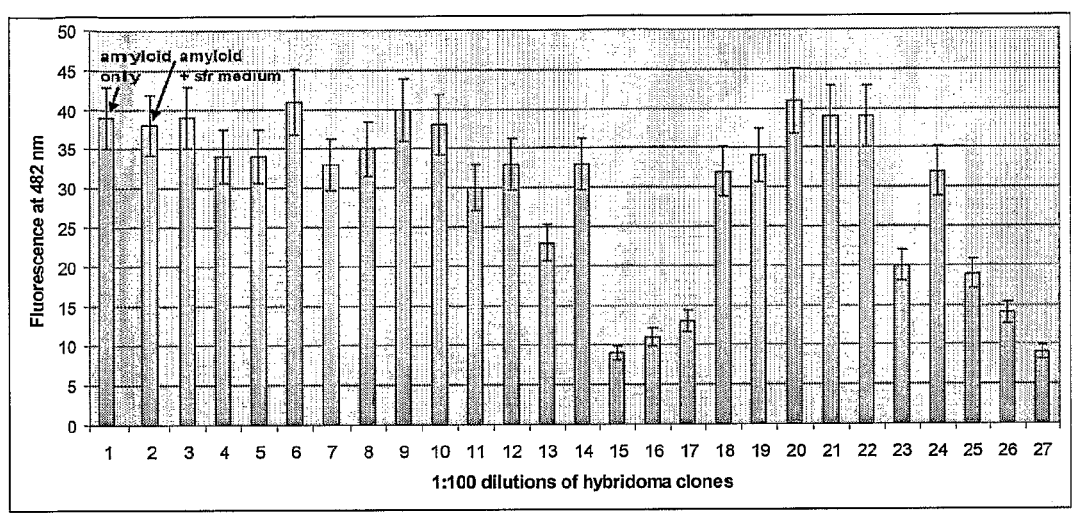
FIG. 9 provides the results of solubilization assay of A$β_{1-42}$ fibers by supernatants of hybridoma clones from palm.-A$β_{1-16}$ immunized C57BL/6 mice. A$β_{1-42}$ fibers formation during 7 days at 37° C. in PBS, pH=7.1. Supernatants were incubated for 24 hrs. sfr medium=medium without FCS. The hybridoma clones were grown in serum free medium for 1 day. Means of 4 samples+SD are shown.

From two palmitoylated Aβ$_{1-16}$/liposomes/lipid A-immunized animals, 25 supernatants were obtained from recently generated hybridoma clones which were shown to be specific for Aβ$_{1-42}$ specific antibodies. They were tested in a solubilization assay according to methods and protocols described in PNAS 2002, 99, 2332-2337. The results are summarized in FIG. 9.

The supernatants of 5 hybridoma clones were found to be able to solubilize β-amyloid fibers in vitro to an extent of up to 75%. The two best clones 15 and 27 were chosen for the purification of monoclonal antibodies. They are being used for further investigations as positive control mAbs in vivo.

EXAMPLE 5

Investigation of the β-sheet to α-helix Transition of the Aβ$_{1-42}$-peptide by Solid State NMR Spectroscopy To avoid loss of $^{13}$C-labelled amino acids the synthesis of the Aβ$_{1-42}$ by Fmoc peptide synthesis was verified by a test-synthesis without labeled amino acids. The identity of the obtained Aβ$_{1-42}$ peptide could be verified by MALDI mass spectroscopy and a purification procedure using HPLC with a reversed phase column and an ammonia buffered acetonitrile water gradient[4] could be established.

The successful setup of a protocol for synthesis and purification of the amyloid β-peptide is followed by the synthesis of the labeled peptide including a $^{13}$C labeled valine at position 12 ($^{12}$val) and a $^{13}$C labeled tyrosine at position 10 ($^{10}$tyr).

Figure 10:
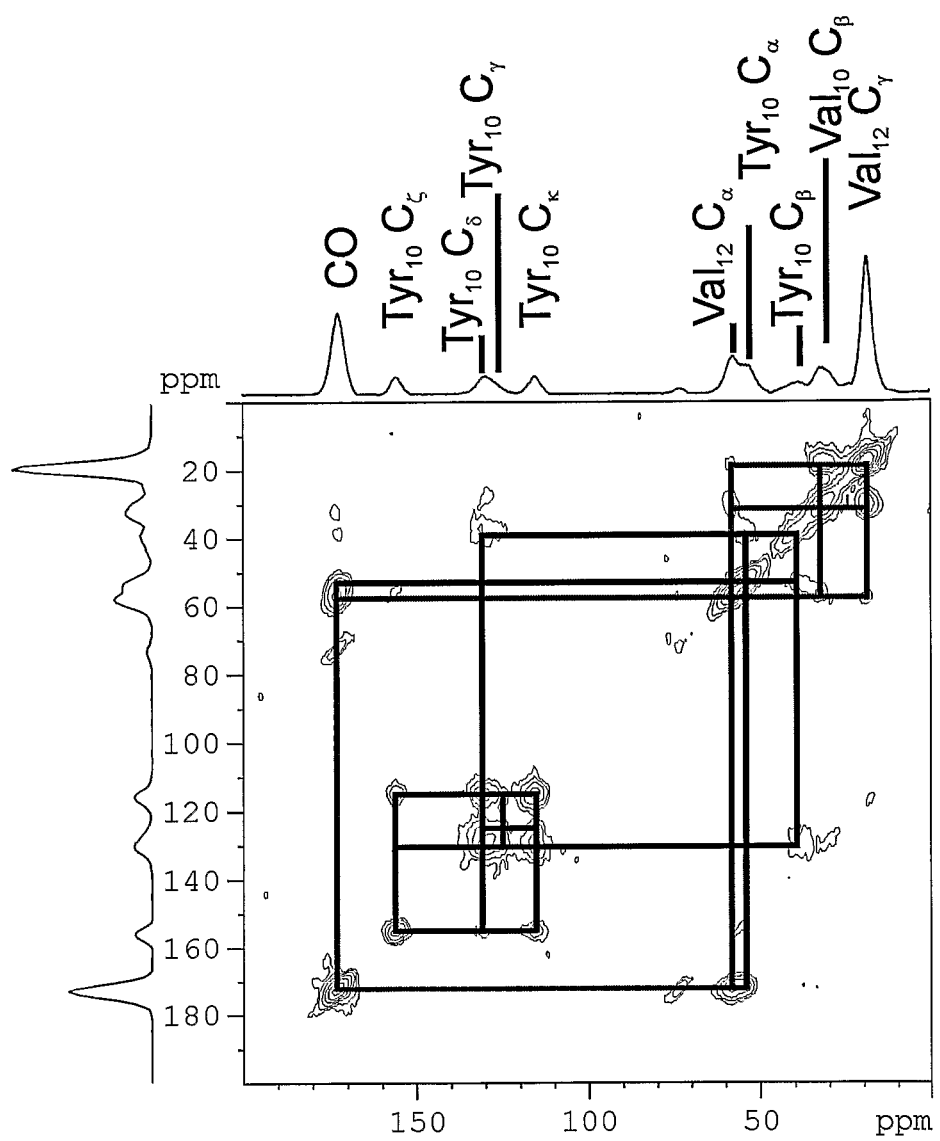
FIG. 10 provides $^{13}C$—$^{13}C$ correlation spectrum of amyloid fibres made of the amyloid β-peptide labeled at $^{10}$Tyr and $^{12}$Val.

The labeled Aβ$_{1-42}$ was used to generate fibers by incubating the peptide solution in PBS buffer for one week at 37° C. $^{13}$C NMR spectra of the lyophilized fibers confirm the β-sheet structure and are in agreement with published results. Incubation of the fibers with Aβ$_{1-16}$ specific antibody for 2 days did not show a significant change $^{13}$C spectrum. First assessments of NMR measurements indicate a change in the secondary structure (FIG. 10).

EXAMPLE 6

Antibodies Elicited by Supramolecular Antigenic Constructs

Manufacturing of the mAbs: Liposomal antigens were prepared as described (Nicolau et al., 2002, PNAS, 99, 2332-37). The sequences PEG-Aβ$_{1-15}$, -Aβ$_{1-16}$, Aβ$_{4-11}$ -Aβ$_{22-35}$ and Aβ$_{29-40}$ were reconstituted in a construct consisting of liposomes made of dimyristoyl phosphatidyl choline (DMPC), dimyristoyl phosphatidyl ethanolamine (DMPEA), dimyristoyl phosphatidyl glycerol (DMPG) and cholesterol (0.9:0.1:0.1:0.7 molar ratios) containing monophosphoryl lipid A (40 mg/mM phospholipids). These antigens and palmitoylated Aβ$_{1-16}$ were used for the immunization in C57BL/6 mice in 2 week intervals. 10-12 animals were immunized with each antigen. After 3 to 6 boostings, mice with therapeutic titers (when a 1:5,000 dilution of the sera were positive in ELISA) were selected for a fusion. The fusion of the mice's B-lymphocytes from the spleens were conducted with the myeloma cell line SP2-0. IgG producing hybridoma clones were selected and tested for their specific binding to the Aβ$_{1-42}$ peptide by ELISA.

Figure 11:
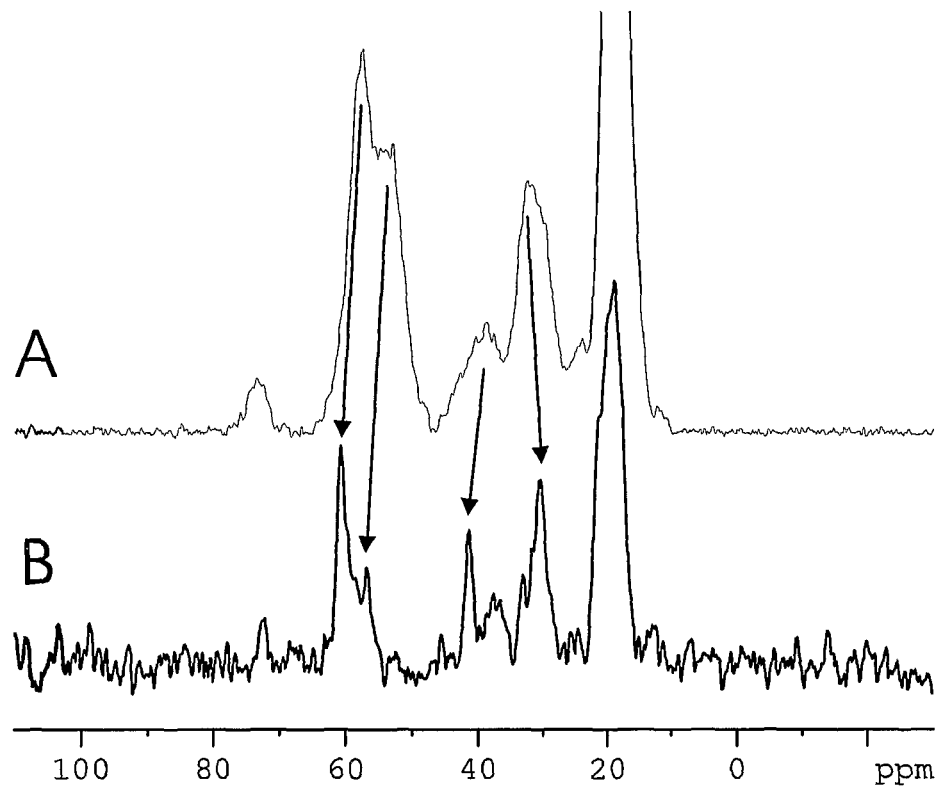
FIG. 11 provides projection of the $^{13}C$—$^{13}C$ correlation spectrum of Aβ-peptide fibers (A) and after incubation with the antibody for 12 days (B).
Figure 12:
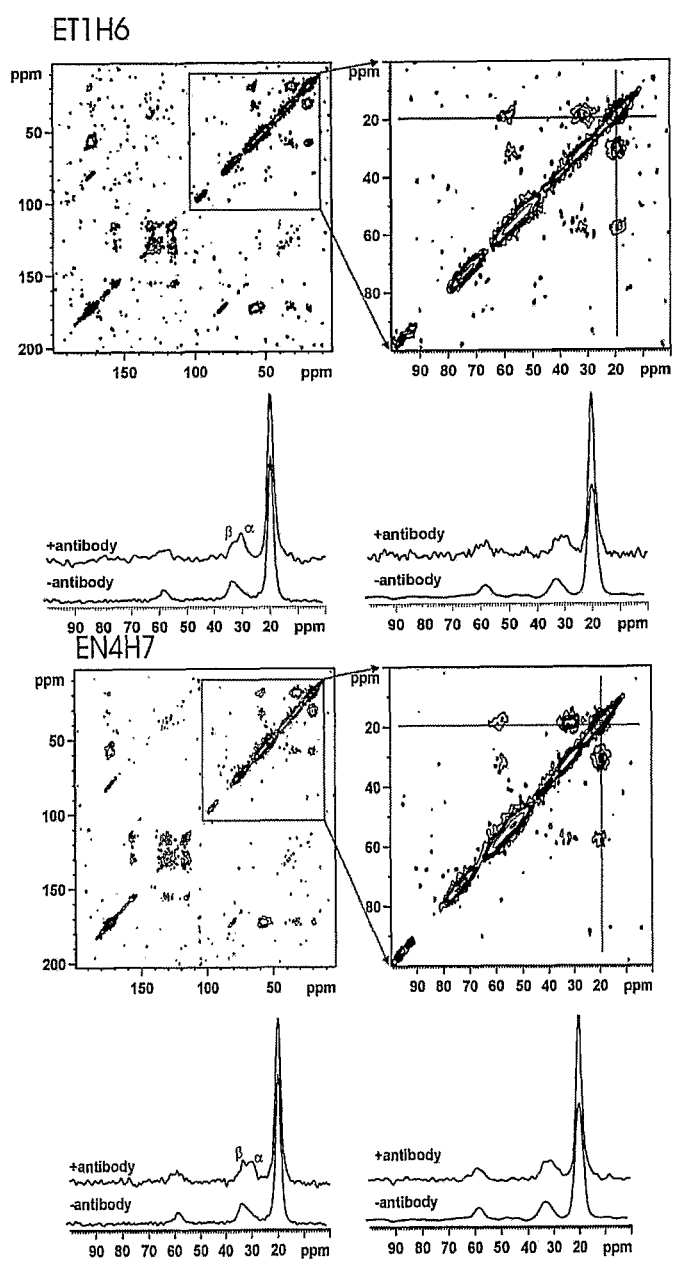
FIG. 12 provides NMR spectra data for assessing the effect of monoclonal antibodies on amyloid beta fibers.

Characterization of the mAb: Disaggregation assays, NMR-studies, QELS- and SPR-measurements were used for the characterization of the mAbs. The mAbs showed a disaggregation of preformed amyloid fibers of up to 80% (Table 1). A transition of β-sheet to α-helix of amyloid was observed induced by the antibodies (FIGS. 11, 12). The measurements by Quasi Elastic Light Scattering (QELS) showed that incubation of amyloid fibers with the monoclonal antibodies resulted in fibers with a size of ≤800 nm, (40-60% of all the fibers present) while amyloid alone gave only very large aggregates (>4 μm).

TABLE 1 mAb obtained by immunization of PEG-Aβ$_{1-15}$, -Aβ$_{4-11}$ and Palm-Aβ$_{1-16}$

| Antigen | Mab/hbridoma | dissagregation [%] | dissociation constants |
|---|---|---|---|
| PEG Aβ$_{1-15}$ | ET-1H6 | 75 | nd |
| PEG Aβ$_{1-15}$ | ET-7E3 | 55 | 2 × 10$^{-7}$ |
| PEG Aβ$_{4-11}$ | EN-4H7 | 80 | nd |
| PEG Aβ$_{4-11}$ | EN-9H2 | 35 | nd |
| Palm Aβ$_{1-16}$ | EJ-1A9 | 55 | 8 × 10$^{-8}$ |
| Palm Aβ$_{1-16}$ | EJ-7H3 | 60 | 7 × 10$^{-8}$ |
| Palm Aβ$_{1-16}$ | AN9C-E4 | 60 | nd |

NMR studies: In order to assess the effect of the mAb on fibers a solution of Aβ-fibers was incubated with the antibody for 12 days. Proton Driven Spin Diffusion measurements (PDSD) were performed to measure a 2D $^{13}$C—$^{13}$C correlation spectrum. FIGS. 11-13 provide NMR data and analysis: NMR: $^{13}$C—$^{13}$C correlation spectrum of Amyloid β-peptide fibers before and after incubation with EN4H7, ET-1H6 or AN9C-E4 for 12 days (A, B). Column (D) and a row (C) extracted of the correlation spectrum. The spectrum (−antibody) shows a spectrum of the pure fibres whereas (+antibody) shows a spectrum in presence of the mAb.

$^{13}$C spectra of the lyophilized fibres enables the assignment of the resonances. The chemical shift values of C$_{60}$ and C$_β$ of Val12 and Tyr10 confirms the β-sheet structure of the pure fibres. (FIG. 11) The shifts of the resonances of the C$_α$ and of the C$_β$ nucleus of $^{12}$Val clearly indicate a transition from β-sheet to α-helix. The shift of the resonance of C$_α$ and C$_β$ of Tyr 10 on the other hand does not clearly indicate a transition of the secondary structure. The behavior fo the Tyr10 resonance can be explained by a model where Tyr10 is at the interface between a β-sheet section and a loop section of the Aβ-peptide in amyloid fibers.

In a second experiment 13C-enriched fibers were incubated with EN4H7 and ET1H6 antibodies (see Table 1) for 12 days. The incubated fibers exhibit shifts of the resonances of the C$_β$ nucleus of $^{12}$Val from 32 ppm to 28 ppm, indicating a transition from β-sheet to α-helix for a significant fraction of the peptide (FIGS. 12 and 13) for both antibodies. The resonances of C$_α$ and C$_β$ for $^{10}$Tyr get broad in the presence of the antibodies. This indicates a transition to a rather unstructured confirmation for the position of $^{10}$Tyr.

EXAMPLE 7

Comparison of Immunogenicity of PEGylated and Palmitoylated Antigens Tested in ELISA ELISA data showed that liposomal PEG-A$\beta_{1-16}$ is more immunogenic than palmitoylated A$\beta_{1-16}$ (FIG. 14). Additional ALUM did not enhance the immunogenicity of PEG-A$\beta_{1-16}$ in the mice. With the exception of the antibody response induced by PEG-A$\beta_{4-11}$, which was slower in comparison to PEG-A$\beta_{1-16}$, in general pegylated peptides appear to be more immunogenic than palmitoylated peptides (FIG. 14).

EXAMPLE 8

Behavioral Tests for Evaluating Efficacy of Antibodies

In order to evaluate the efficacy of antibodies elicited by the methods described herein, namely elicited by use of supramolecular antigenic constructs comprising modified amyloid peptides (such as pegylated amyloid peptides), mice will be treated and then evaluated using the behavior tests outlined below.

Morris Water Maze

The pool (a white, circular vessel 1 m in diameter) contains water at 20° C. with titanium-dioxide as an odorless, nontoxic additive to hide the escape platform (1 cm beneath the water level). Swimming of each mouse is videotaped and analyzed (Ethovision, Noldus information Technology, Wageningen, the Netherlands). Prior to training, each mouse is placed on top of the platform for 15 seconds. For place navigation tests, mice are trained to locate the hidden platform in five blocks of three trials over three consecutive days. Each trial consists of a forced swim test of maximum 120 seconds, followed by 60 seconds of rest. The time each mouse needed for location of the platform is measured. The five consecutive trials result in a learning curve.

24 hours after the last training, each animal has a probe trial with the platform removed. Mice are allowed to search for 60 seconds and quadrant search time and crossings of the original platform position is measured.

Mice that refuse to swim and search the platform, but instead wait until the performer takes them out of the pool, the so-called "floaters" are to be excluded from analysis.

Open Field

A Plexiglas open-field box (52×52×40 cm) with black vertical walls and a translucent floor, dimly illuminated by a lamp placed underneath the box is used for the test. Different areas are allocated by a computerized system (Ethovision, Noldus information Technology, Wageningen, the Netherlands): the corners (9×9 cm), the four sides of the box (9 cm from wall) and the center of the open field box (43×43 cm). Each mouse is videotaped and the activity is analyzed (Ethovision) by measuring the distance (cm) of the track, the velocity (cm/sec) of the mouse, the duration/time (sec) spent in the center compared to the border (corners+sides) and the frequency (N) of crossings between both areas. Each mouse is placed in the middle of the box and is allowed to explore the box for ten minutes. In between tests the open-field box is cleaned and dried before the introduction of a new mouse.

Novel Object Recognition Test

Mice are familiarized for one hour to a Plexiglas open-field box (52×52×40 cm) with black vertical walls and a translucent floor, dimly illuminated by a lamp placed underneath the box. The next day the animals are placed in the same box and submitted to a 1O minutes acquisition trial. During this trial mice are placed individually in the open field in the presence of object A (blue ball or red cube, similar sized of ±4 cm), and the frequency exploring object A (when the animals snout is directed towards the object at a distance of <1 cm and the mice are actively sniffing in the direction of the object) is recorded (Freq$_{AA}$). During a 10 minutes retention trial (second trial) which is performed 3 hours later, a novel object (object B, red cube or blue ball) is placed together with the familiar object (object A) into the open field. The frequency the animal explored the two objects is recorded (Freq$_A$ and Freq$_B$).

The recognition index (RI) defined as the ratio of the frequency in which the novel object is explored over the frequency in which both objects were explored [Freq$_B$/(Freq$_A$+Freq$_B$)×100] is used to measure non-spatial memory. The frequency object A is explored during the acquisition trial is used to measure curiosity.

References

1. C. Nicolau, R. Greferath, T. S. Balaban, J. Lazarte and R. Hopkins (2002). Proc. Natl. Acad. Sci. USA. 99,2332-2337.
2. Fluka A G (2002) Cat. #79898.
3. P.-F. Tosi, D. Radu, and C. Nicolau (1995). Biochem. Biophys. Res. Chem. 212, 494-500.
4. Fukuda H, Shimizu T, Nakajima M, Mori H, Shirasawa T. *Bioorg. Med. Chem. Lett.* 1999; 9: 953-956
5. Petkova A T, Ishii Y, Balbach J J, Antzutkin O N, Leapman R D, Delaglio F, Tycko R. *Proc. Natl. Acad. Sci. U.S.A* 2002; 99: 16742-16747

We claim:

1. A method for restoring memory and curiosity awakening in a patient suffering from Alzheimer's disease comprising administering to a patient in need thereof a supramolecular antigenic construct comprising an antigenic peptide modified with hydrophobic moieties and reconstituted in a liposome, wherein the antigenic peptide is an Aβ peptide selected from the group consisting of SEQ ID NOs: 1-5.

2. The method of claim 1, wherein the hydrophobic moieties are, palmitic acid, poly-amino acids, poly-glycine, poly-histidine, poly-saccharides, polygalacturonic acid, polylactic acid, polyglycolide, chitin, chitosan, synthetic polymers, polyamides, polyurethanes, polyesters, co-polymers or poly (methacrylic acid) and N-(2-hydroxy)propyl methacrylamide.

3. The method of claim 1, wherein the liposomes consist of phospholipids and cholesterol.

4. The method of claim 1, wherein the supramolecular antigenic construct further comprises a pharmaceutical carrier.

5. The method of claim 1, wherein the patient is an animal or human.

6. The method of claim 2, wherein said hydrophobic moieties are fatty acids, triglycerides or phospholipids, wherein a fatty acid carbon backbone of the hydrophobic moieties comprises at least 10 carbon atoms.

7. The method of claim 6, wherein the fatty acid carbon backbone has at least 14 and up to 24 carbon atoms.

8. The method of claim 1, wherein the antigenic peptide is further modified to have a polyethylene glycol covalently attached at each N- and C-terminus, and wherein the hydrophobic moieties are covalently attached to each free PEG terminus and insert into the liposome bilayer.

* * * * *